(12) United States Patent
Mikayama et al.

(10) Patent No.: US 7,063,845 B2
(45) Date of Patent: Jun. 20, 2006

(54) HUMAN ANTI-CD40 ANTIBODIES

(75) Inventors: Toshifumi Mikayama, Takasaki (JP);
Nobuaki Takahashi, Takasaki (JP);
Xingjie Chen, San Diego, CA (US);
Stephen P. Schoenberger, Encinitas, CA (US)

(73) Assignees: Gemini Science, Inc., San Diego, CA (US); La Jolla Institute for Allergy & Immunology, San Diego, CA (US)

( * ) Notice: Subject to any disclaimer, the term of this patent is extended or adjusted under 35 U.S.C. 154(b) by 389 days.

(21) Appl. No.: 09/844,684

(22) Filed: Apr. 27, 2001

(65) Prior Publication Data

US 2002/0142358 A1 Oct. 3, 2002

Related U.S. Application Data

(60) Provisional application No. 60/200,601, filed on Apr. 28, 2000.

(51) Int. Cl.
  *A61K 39/395*    (2006.01)
  *C07K 16/28*     (2006.01)
  *C12N 15/13*     (2006.01)
  *C12N 5/10*      (2006.01)

(52) U.S. Cl. ............... 424/153.1; 424/130.1; 424/133.1; 424/135.1; 424/141.1; 424/142.1; 424/143.1; 424/144.1; 424/173.1; 435/326; 435/327; 435/332; 435/334; 435/343; 435/343.1; 530/387.1; 530/388.1; 530/388.15; 530/388.2; 530/388.22; 530/388.7; 530/388.73; 536/23.1; 536/23.5; 536/23.53

(58) Field of Classification Search ......... 424/130.1, 424/132.1, 143.1; 435/326, 334; 530/387.1, 530/388.2, 388.73; 536/23.1
See application file for complete search history.

(56) References Cited

U.S. PATENT DOCUMENTS

| | | | |
|---|---|---|---|
| 5,677,165 A | 10/1997 | de Boer et al. | |
| 5,786,456 A | 7/1998 | Ledbetter et al. | |
| 5,801,227 A | 9/1998 | Fanslow, III et al. | |
| 5,874,082 A | * 2/1999 | De Boer | |
| 6,004,552 A | 12/1999 | de Boer et al. | 424/144.1 |
| 6,051,228 A | 4/2000 | Aruffo et al. | 424/144.1 |
| 6,150,584 A | * 11/2000 | Kucherlapati et al. | |

FOREIGN PATENT DOCUMENTS

| | | |
|---|---|---|
| EP | 0945 465 A1 | 9/1999 |
| EP | 0972 445 A1 | 1/2000 |
| WO | WO 91/09115 | 6/1991 |
| WO | WO 96/33735 | 10/1996 |
| WO | WO 96/34096 | 10/1996 |
| WO | WO 99/42075 | 8/1999 |
| WO | WO 99/61051 | 12/1999 |
| WO | WO 00/00156 | 1/2000 |
| WO | WO 00/75348 A1 | 12/2000 |
| WO | WO 00/75348 A1 | 12/2000 |
| WO | WO 01/24823 | 4/2001 |
| WO | WO 01/56603 | 8/2001 |
| WO | WO 01/83755 A3 | 11/2001 |
| WO | WO 01/83755 A2 | 11/2001 |
| WO | WO 02/28904 A2 | 4/2002 |
| WO | WO 02/28904 | 4/2002 |

OTHER PUBLICATIONS

Tomizuka, et al., "Double trans–chromosomic mice: Maintenance of two individual human chromosome fragments containing Ig heavey and kappa loci and expression of fully human antibodies", PNAS, Jan. 18, 2000, vol. 97, No. 2.

Schoenberger, et al., "T–cell help for cytotoxic T lymphocytes is mediated by CD40–CD40L interactions", Nature, vol. 393, Jun. 4, 1998.

Stamenkovic, et al., "A B–lymphocyte activation molecule related to the nerve growth factor receptor and inuced by cytokines in carcinomas", The EMBO Journal, vol. 8, No. 5, pp. 1403–1410, 1989.

Clark, et al., "CDw40 and BLCa–specific monoclonal antibodies detect two distinct molecules which transmit progression signals to human B lymphocytes*", Eur. J. Immunol., 1988, 18: 451–457.

Ledbetter, et al., Augmentation of Normal and Malignant B Cell Proliferation by Monoclonal Antibody to the B Cell–Specific Antigen BP50 (CDW40), The Journal of Immunology, vol. 138, pp. 788–794, No. 3, Feb. 1, 1987.

Clark, et al., "Activation of human B cells mediated through two distinct cell surface differentiation antigens, Bp35 and Bp50", Proc. Natl. Acad. Sci. USA, vol. 83, pp. 4494–4498, Jun. 1986.

Paulie, et al., "A p50 surface antigen restricted to human urinary bladder carcinomas and B lymphocytes", Cancer Immunology Immunother, (1985), 20: 23–28.

Kwekkeboom, et al., "Helper effector function of human T cells stimulated by anti–CD3 mAb can be enhanced by co–stimulatory signals and is partially dependent on CD40–CD40 ligand interaction," *Eur. J. Immunol*, (1994), vol. 24, pp. 508–517.

Hasbold, et al., "Cell division number regulates IgG1 and IgE switching of B cells following stimulation by CD40 ligand and IL–4," *Eur. J. Immunol*. (1998), vol. 28, pp. 1040–1051.

(Continued)

*Primary Examiner*—Phillip Gambel
(74) *Attorney, Agent, or Firm*—Pillsbury Winthrop Shaw Pittman LLP

(57) ABSTRACT

The invention is directed to human antibodies that bind CD40 (e.g., human CD40), methods of producing the antibodies and methods of use. Invention human CD40 antibodies include antibodies that can modulate one or more activities of CD40, such as increasing or decreasing cell proliferation. Invention human CD40 antibodies are therefore useful for increasing or decreasing a CD40 activity in order to alter CD40 activity in vivo.

30 Claims, 6 Drawing Sheets

OTHER PUBLICATIONS

Pound, et al., "Minimal cross–linking and eptiope requirements for D40–dependent suppression of apoptosis contrast with those for promotion of the cell cycle and homotyic adhesions in human B cells," *Int'l Immunol.* (1999), vol. 11, No. 1, pp. 11–20.

Francisco, et al., "Agonistic Properties and in vivo Antitumor of the Anti–CD40 Antibody SGN–14," *Cancer Research*, (Jun. 15, 2000), vol. 60, pp. 3225–3231.

Roamno, et al., "Triggering of CD40 Antigen Inhibits Fludarabine–Induced Aoptosis in B Chronic Lymphocytic Leukemia Cells," *Blood*, (Aug. 1, 1998) vol. 98, No. 3, pp. 990–995.

Hirano, et al., "Inhibition of Human Breast Carcinoma Growth by a Soluble Recombinant Human CD40 Ligand," *Blood*, (May 1, 1999), vol. 93, No. 9, pp. 2999–3007.

Francisco, et al., "Construction, Expression, and Characterization of BD1–G28–5 sFv, a Single–chain Anti–CD40–Immunotoxin Containing the Ribosome—of BD—in activating Protein Bryodin 1," *Journal of Biological Chemistry*, (Sep. 26, 1997), vol. 272, No. 39, pp. 24165–24169.

Maxwell, et al., "Contrasting the Roles of Costimulation and the Natural Adjuvant Lipopolysaccharide During the Induction of T Cell Immunity," *J. Immunol.*, (May 1, 2002), vol. 168, No. 9, pp. 4372–4381.

Simonsson, et al., "Single, Antigen–Specific B Cells Used to Generate Fab Fragments Using CD40–Mediated Amplification or Direct PCR Cloning," *BioTechniques*, (1995), vol. 18, No. 5, pp. 862–869.

Duliforce, et al., "Enhancement of T cell–independent immune responses in vivo by CD 40 antibodies," *Nature Medicine*, (Jan. 1998), vol. 4, No. 1, pp. 88–91.

Erickson, et al., "Short–circuiting long–lived humoral immunity by the heightened engagement of CD40," *The J. of Clinical Investigation*, (Mar., 2002), vol. 109, No. 5, pp. 613–620.

Murphy, et al., "Antibodies to CD40 Prevent Epstein–Barr Virus– Mediated Human B–Cell Lymphomagenesis in Severe Combined Immune Deficient Mice Given Human Peripheral Blood Lymphocytes," *Blood*, (Sep. 1, 1995), vol. 86, No. 5, pp. 1946–1953.

Funakoshi, et al., "Differential in vitro and in vivo Antintumor Effects Mediated by Anit–CD40 and Anti–CD20 Monoclonal Antibodies Against Human B–Cell Lyphomas," *J. of Immunology*, (1996) vol. 19, No. 2, pp. 93–101.

Schwabe, et al., "Modulation of Soluble CD40 Ligand Bioactivity with Anti–CD40 Antibodies," *Hybridoma*, (1997), vol. 16, No. 13, pp. 217–226.

Funakoshi, et al., "Inhibition of Human B–Cell Lymphoma Growth by CD40 Stimulation," *Blood*, (May 15, 1994), vol. 83, No. 10, pp. 2787–2794.

Rolink, et al., "The SCID but Not the RAG–2 Gene Product Is Required for Sμ–Sε Heavy Chain Class Switching," *Immunity*, (Oct., 1996) vol. 5, pp. 319–330.

Kwekkeboom, et al., "CD40 plays and essential role in the activation of human B cells by murine EL4B5 cells," *Immunology*, (1993), vol. 79, pp. 439–444.

Zhou, et al., "An Agonist Anti–Human CD40 Monoclonal Antibody that Induces Dendritic Cell Formation and Maturation and Inhibits Proliferation of a Myeloma Cell Line," *Hybridoma*, vol. 18, No. 6, 1999, pp. 471–478.

Heath, et al., "Monoclonal antibodies to murine CD40 define two distinct functional epitopes," *Eur. J. Immunology*, (1994) vol. 24, pp. 1828–1834.

Mazzei, et al., "Recombinant Soluble Trimeric CD40 Ligand Is Biologically Active," *Journal of Biological Chemistry*, (Mar. 31, 1995), vol. 270, No. 13, pp. 7025–7028.

Hasbold, et al., "Properties of mouse CD40: cellular distribution of CD40 and B cell activation by monoclonal anti––mouse CD40 antibodies," *Eur. J. Immunology.*, (1994) vol. 24, pp. 1835–1842.

Weng, et al., "Human Anti–CD40 Antagonistic Antibodies Inhibit the Proliferation of Human B Cell Non–Hodgkin's Lymphoma," Program of the 43$^{rd}$ Annual Meeting of The American Society of Hematology, (Dec. 7–11, 2001), Abstract No. 1947, p. 466a.

Ledbetter, et al., "Agonistic Activity of a CD40–Specific Single–Chain Fv Constructed from the Variable Regions of mAb G28–5," *Critical Reviews in Immunology*, (1997), vol. 17, pp. 427–435.

de Boer, et al., "Generation of monoclonal antibodies to human lymphocyte cell surface antigens using insect cells expressing recombinant proteins," *Journal of Immunological Methods*, (1992) vol. 152, pp. 15–23.

Karlsson, et al., "Selection of human single chain antibodies against CD–40," *Immunology Letters*, vol. 73, Nos. 2,3, Abstract No. 358.

Sotomayor, et al., "Conversion of tumor–specific CD4 T–cell tolerance to T–cell priming through in vivo ligation of CD40," *Nature*, (Jul., 1999), vol. 5, No. 7, pp. 780–787.

Diehl, et al., "CD40 activation in vivo overcomes peptide–induced peripheral cytotoxic T–lymphocyte tolerance and augments anti–tumor vaccine efficacy," *Nature Medicine*, (Jul. 1999) vol. 5, No. 7, pp. 774–779.

Schoenberger, et al., "T–cell help for cytotoxic T lymphocytes is mediated by CD40–CD40L interactions," *Nature*, (Jun. 4, 1998), vol. 393, pp. 480–483.

Van Mierlo, et al. "CD40 stimulation leads to effective therapy of CD40–tumors through induction of strong systemic cytotoxic T lymphocyte immunity," *PNAS*, (Apr. 16, 2002) vol. 99, No. 8, pp. 5561–5566.

An, et al., "Ligation of CD40 Potentiates Fas–Mediated Activation of the Cysteine Protease CPP32, Cleavage of Its Death Substrate PARP, and Apoptosis in Ramos—Burkitt Lymphoma B Cells," *Cellular Immunology*, (1997) vol. 181, pp. 139–152.

Barr, et al., "Functional activity of CD40 antibodies correlates to the position of binding relative to CD154," *Immunology*, (2001) vol. 102, pp. 39–43.

Baccam, et al., "Membrance–bound CD154, but not CD40–specific antibody, mediates NF–xB–independent IL–6 production in B cells," *Er. J. Immunol.*, (1999), vol. 29, pp. 3855–3866.

Kedl, et al., "CD40 stimulation accelerates deletion of tumor specific CD8+ T cells in the absence of tumor–antigen vaccination," *PNAS*, (Sep. 11, 2001) vol. 98, No. 19, pp. 10811–10816.

Tomizuka, et al., "Double trans–chromosomic mice: Maintenance of two individual human chromosome fragments containing Ig heavy and k loci and expression of fully human antibodies," *PNAS*, (Jan. 18, 2000) vol. 97, No. 2, pp. 722–727.

Boon, et al., "Preclinical assessment of anti–CD40 Mab 5D12 in cynomolgus monkeys," *Toxicology*, (2002), vol. 174, pp. 53–65.

* cited by examiner

FL1-H

FL2-H

FL2-H

FL2-H

FL2-H

SEQUENCE LISTING

```
<160> NUMBER OF SEQ ID NOS: 15

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 1
cccagatctg tccatccaga accacccact gcatgcagag                    40

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 2
acaagatctg ggctctacgt atctcagccg atcctgggga c                  41

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 3
```

```
gtgcacgccg ctggtcaggg cgcctg                                          26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 4
gttgaagctc tttgtgacgg gcgagc                                          26

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5
accgtgtcga cggtgatcag gactgaacag                                      30

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 6
accgtgtcga cgctgatcag gactgcaca                                       29

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
agtgctagct gaggagacgg tgac                                            24

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
aactccagat ctagggcaag cagtggtaac                                      30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
tatcccgtac ggttgatctc caccttggtc                                      30

<210> SEQ ID NO 10
<211> LENGTH: 520
<212> TYPE: DNA
```

<210> SEQ ID NO 10
<211> LENGTH: (not shown)
<212> TYPE: DNA
<213> ORGANISM: Homo sapiens

<400> SEQUENCE: 10

```
gctgatcagg actgcacaca gagaactcac catggagttt gggctgagct gggttttcct      60
tgttgctatt ttaaaaggtg tccagtgtga ggtgcagctg gtggagtccg ggggaggctt     120
agttcagcct ggggggtccc tgagactctc ctgtgcagtc tctggattca ccttcagtac     180
ctactggatg cactgggtcc gccaagctcc agggaagggg ctggtgtggg tctcacgtat     240
taatagtgat gggagtagca aacctacgc ggactccgtg aagggccgat tcaccatctc      300
cagagacaac gccaagaaca cgctgtatct gcaaatgaac agtctgagag ccgaggacac     360
ggctgtgtat tactgtgcaa gagatagagt actatggatc ggggagttat cctactacgg     420
tatgggcgtc tggggccaag gaccacggt caccgtctcc tcagctagca ccaagggccc     480
atcggtcttc cccctggcac cctcctccaa gagcacctct                           520
```

<210> SEQ ID NO 11
<211> LENGTH: 698
<212> TYPE: DNA
<213> ORGANISM: Homo sapiens

<400> SEQUENCE: 11

```
ggggagtcag acccagtcag gacacagcat ggacatgagg gtccccgctc agctcctggg      60
gctcctgctg ctctggctcc caggtgccaa atgtgacatc cagatgaccc agtctccttc     120
caccctgtct gcatctgtag gagacagagt caccatcact tgccgggcca gtcagagtat     180
tagtaactgg ttggcctggt atcagcagaa accagggaaa gcccctaagc tcctgctcta     240
taaggcatct ggtttagaaa gtggggtccc atcaaggttc agcggcagtg gatctgggac     300
agaattcact ctcaccatca cagcctgca gcctgatgat tttgcaactt attactgcca     360
acagtctaat agttattcgt ggacgttcgg ccacgggacc aaggtggaaa tcaaacgtac     420
ggtggctgca ccatctgtct tcatcttccc gccatctgat gagcagttga aatctggaac     480
tgcctctgtt gtgtgcctgc tgaataactt ctatcccaga gaggccaaag tacagtggaa     540
ggtggataac gcccctccaa tcggtaactc ccaggagagt gtcacagagc aggacagcaa     600
ggacagcacc tacagcctca gcagcaccct gacgctgagc aaagcagact acgagaaaca     660
caaagtctac gcctgcgaag tcacccatca gggcctga                             698
```

<210> SEQ ID NO 12
<211> LENGTH: 580
<212> TYPE: DNA
<213> ORGANISM: Homo sapiens

<400> SEQUENCE: 12

```
ggtgatcagg actgaacagg gagaactcac catggagttt gggctgggct ggcttttct      60
tgtggctatt ttaaaaggtg tccagtgtga ggtgcagctg ttggagtctg ggggaggctt     120
ggtacagcct ggggggtccc tgagactctc ctgtgcagcc tctggattcg cctttagcag     180
ctatgccatg agctgggtcc gccaggctcc agggaagggg ctggagtggg tctcagctat     240
tagtggtagt ggtggtagca catactacgc agactccgtg aagggccggt tcaccatctc     300
cagagacaat tccaagaaca cgctgtatct gcaaatgaac agcctgagag ccgaggacac     360
ggccgtatat tactgtgcga agatggggg gtactatggt tcgggagtt atgggtactt     420
tgactactgg ggccagggaa ccctggtcac cgtctcctca gctagcacca agggcccatc     480
ggtcttcccc ctggcaccct cctccaagag cacctctggg ggcacagcgg ccctgggctg     540
```

```
cctggtcaag gactacttcc ccgaaccggt gacggtgtcg                            580
```

<210> SEQ ID NO 13
<211> LENGTH: 716
<212> TYPE: DNA
<213> ORGANISM: Homo sapiens

<400> SEQUENCE: 13

```
caacgcagag tacgcgggga ggagtcagac ccagtcagga cacagcatgg acatgagggt     60
ccccgctcag ctcctggggc tcctgctgct ctggttccca ggttccagat gcgacatcca    120
gatgacccag tctccatctt ccgtgtctgc atctgcagga gacagagtca ccatcacttg    180
tcgggcgagt cagggtatta gcagctggtt agcctggtat caacagaaac agggaaagc    240
ccctaagctc ctgatctatg ctggatccag tttgcaaagt ggggtcccat caaggttcag    300
cggcagtgga tttgggacag atttcactct caccatcggc agcctgcagc ctgaagattt    360
tgcaacttac tattgtcaac aggctagcag tttccctcgg acgttcggcc aagggaccaa    420
ggtggagatc aaacgtacgg tggctgcacc atctgtcttc atcttcccgc catctgatga    480
gcagttgaaa tctggaactg cctctgttgt gtgcctgctg aataacttct atcccagaga    540
ggccaaagta cagtggaagg tggataacgc cctccaatcg ggtaactccc aggagagtgt    600
cacagagcag gacagcaagg acagcaccta cagcctcagc agcaccctga cgctgagcaa    660
agcagactac gagaaacaca agtctacgc ctgcgaagtc acccatcagg gcctga        716
```

<210> SEQ ID NO 14
<211> LENGTH: 630
<212> TYPE: DNA
<213> ORGANISM: Homo sapiens

<400> SEQUENCE: 14

```
ggtctatata agcagagctg gtacgtcct cacattcagt gatcagcact gaacacagac      60
ccgtcgacgg tgatcaggac tgaacagaga gaactcacca tggagtttgg gctgagctgg    120
cttttcttg tggctatttt aaaaggtgtc cagtgtgagg tgcagctgtt ggagtctggg    180
ggaggcttgg tacagcctgg ggggtccctg agactctcct gtgcagcctc tggattcacc    240
tttagcagct atgccatgag ctgggtccgc caggctccag ggaaggggct ggagtgggtc    300
tcagctatta gtggtagtgg tggtagcaca tactacgcag actccgtgaa gggccggttc    360
accatctcca gagacaattc caagaacacg ctgtatctgc aaatgaacag cctgagagcc    420
gaggacacgg ccgtatatta ctgtgcgaaa gatggggggt actatggttc ggggagttat    480
gggtactttg actactgggg ccagggaacc ctggtcaccg tctcctcagc tagcaccaag    540
ggcccatcgg tcttccccct ggcaccctcc tccaagagca cctctggggg cacagcggcc    600
ctgggctgcc tggtcaagga ctacttcccc                                      630
```

<210> SEQ ID NO 15
<211> LENGTH: 728
<212> TYPE: DNA
<213> ORGANISM: Homo sapiens

<400> SEQUENCE: 15

```
caagcagtgg taacaacgca gagtacgcgg ggggagtcag acccagtcag gacacagcat     60
ggacatgagg gtccccgctc agctcctggg gctcctgctg ctctggttcc caggttccag    120
atgcgacatc cagatgaccc agtctccatc ttccgtgtct ggatctgtag gagacagagt    180
```

```
caccatcact tgtcgggcga gtcagggtat tagcagctgg ttagcctggt atcagcagaa    240
accagggaaa gccgctaagc tcctgatcta tgctggatcc agtttgcaaa gtggggtccc    300
atcaaggttc agcggcagtg gatttgggac agatttcact ctcaccatca gcagcctgca    360
gcctgaagat tttgcaactt actattgtca acaggctagc agtttccctc ggacattcgg    420
ccaagggacc aaggtggaga tcaaacgtac ggtggctgca ccatctgtct tcatcttccc    480
gccatctgat gagcagttga aatctggaac tgcctctgtt gtgtgcctgc tgaataactt    540
ctatcccaga gaggccaaag tacagtggaa ggtggataac gccctccaat cgggtaactc    600
ccaggagagt gtcacagagc aggacagcaa ggacagcacc tacagcctca gcagcaccct    660
gacgctgagc aaagcagact acgagaaaca caaagtctac gcctgcgaag tcacccatca    720
gggcctga                                                             728
```

HUMAN ANTI-CD40 ANTIBODIES

PRIORITY INFORMATION

This application claims priority to U.S. application Ser. No. 60/200,601, filed Apr. 28, 2000.

TECHNICAL FIELD

The invention relates to human antibodies that bind to antigens and, more particularly to human anti-CD40 antibodies that bind to human CD40 that modulate activity of CD40.

BACKGROUND

The immune system serves a vital role in protecting the body against infectious agents. It is well established, however, that a number of disease states and/or disorders are a result of either abnormal or undesirable activation of immune responses. Common examples include graft versus host disease (GVHD), organ or graft rejection, inflammation, and autoimmune linked diseases such as multiple sclerosis (MS), systemic lupus erythematosus (SLE), and rheumatoid arthritis (RA).

In general, an immune response is activated as a result of either tissue injury or infection. Both cases involve the recruitment and activation of a number of immune system effector cells (i.e. B- and T-lymphocytes, macrophages, eosinophils, neutrophils, etc.) in a process coordinated through a series of complex cell-cell interactions. A typical scenario by which an immune response is mounted against a foreign protein is as follows: Foreign proteins captured by antigen presenting cells (APC's) such as macrophages or dendritic cells are processed and displayed on the cell surface of the APC. Circulating T-helper cells ($T_H$ cells), which express an immunoglobulin that recognizes (i.e. binds) the displayed antigen undergo activation by the APC. The activated $T_H$ cells in turn activate appropriate B-cell clones to proliferate and differentiate into plasma cells which then produce and secrete humoral antibodies targeted against the foreign antigen. The secreted antibodies bind to any cells expressing the foreign protein, targeting such cells for destruction by other immune effector cells.

When $T_H$ cells contact B cells this stimulates B cell proliferation and immunoglobulin (Ig) class switching from IgM to IgG, IgA or IgE classes. Various receptor-ligand interactions are involved in mediating contact between a $T_H$ cell and a B cell during the response to a T-dependent antigen. In particular, CD40—CD40 ligand (CD40L) pairing is critical to achieving this cell-cell interaction. CD40L is not expressed on resting $T_H$ cells but is induced after the cell contacts T-dependent antigen. The B cell is stimulated by CD40L through the CD40 antigen on the B-cell surface and, in combination with IL-4, mediates the secretion of IgE.

CD40L and CD40 are both transmembrane glycoproteins within the family of tumor necrosis factor (TNF) and TNF receptors, (TNF-R), respectively. Human CD40 is a peptide of 277 amino acids having a molecular weight of 30,600, a 19 amino acid secretory signal peptide comprising predominantly hydrophobic amino acids and cysteine-rich motifs in the extracellular region. The protein contains a putative leader sequence, transmembrane domain and a number of other features common to membrane-bound receptor proteins.

Human CD40L is a type II membrane-bound glycoprotein (Spriggs et al., J. Exp. Med. 176:1543 (1992)). Murine CD40L has also been cloned (Armitage et al., Nature 357:80 (1992)). CD40L has an extracellular region at its C-terminus, a transmembrane region and an intracellular region at its N-terminus. Soluble CD40L comprises an extracellular region of CD40L (amino acid 47 to amino acid 261). CD40L induces B-cell proliferation in the absence of any co-stimulus, and can also induce production of immunoglobulins in the presence of cytokines. CD40L activity is mediated by binding of the extracellular region of CD40L with CD40.

CD40 is expressed on B lymphocytes and participates in many B cell functions in addition to inducing Ig class-switching, such as acting as a cofactor with specific antigen and certain lymphokines for B cell mitogenesis, preventing apoptotic cell death and triggering B cell adhesion to other cells. CD40 is also expressed on cell types other than B-cells, including macrophages, dendritic cells, thymic epithelial cells, Langerhans cells, and endothelial cells. These findings have led to the current belief that CD40 plays a broad role in immune regulation by mediating interactions of T-cells with B-cells as well as with other cell types. In support of this notion, stimulation of CD40 in macrophages and dendritic cells is required for T-cell activation during antigen presentation (Gruss et al., Leuk. Lymphoma, 24:393 (1997)).

Evidence indicates that CD40 participates in tissue inflammation as well. Production of the inflammatory mediators IL-12 and nitric oxide by macrophages have been shown to be CD40 dependent (Buhlmann and Noelle, J. Clin. Inmunol. 16:83 (1996)). In endothelial cells, stimulation of CD40 by CD40L has been found to induce surface expression of E-selectin, ICAM-1, and VCAM-1, promoting adhesion of leukocytes to sites of inflammation (Buhlmann and Noelle, J. Clin. Immunol., 16:83 (1996); Gruss et al., Leuk. Lymphoma, 24:393 (1997)). Finally, studies of CD40 overexpression in epithelial and hematopoietic tumors as well as tumor infiltrating endothelial cells indicate that CD40 may play a role in tumor growth and/or angiogenesis (Gruss et al., Leuk. Lymphoma, 24:393 (1997); Kluth et al., Cancer Res., 57:891 (1997)).

Due to the role that CD40 plays in humoral immunity therapeutic strategies aimed at modulating CD40 can be useful in treating a number of immune associated disorders. For example, inhibition of CD40 activity could reduce graft-versus-host disease (GVHD), graft rejection, and autoimmune diseases such as multiple sclerosis (MS), systemic lupus erythematosus (SLE), and certain types of arthritis. CD40 inhibitors may also be useful as an anti-inflammatory compound, and could therefore be useful in treating a variety of inflammatory and allergic conditions such as asthma, rheumatoid arthritis, allograft rejections, inflammatory bowel disease, various dermatological conditions, and psoriasis. Inhibitors of CD40 may be useful as anti-tumor agents and inhibitors of other hyperproliferative conditions as well.

Promoters or stimulators of CD40 activity may be useful for increasing humoral immunity to resist an infectious agent, such as a viral or bacterial pathogen. Promoters may also be useful in stimulating or potentiating humoral immunity against tumors. In addition, promoters or stimulators of CD40 activity may be useful in promoting memory thereby improving the rapidity or robustness of the immune response.

Monoclonal antibodies directed against either CD40 or CD40L in animal models indicate that inhibition of CD40 stimulation would have therapeutic benefit for GVHD, allograft rejection, rheumatoid arthritis, SLE, MS, and B-cell lymphoma (Buhlmann and Noelle, J. Clin. Immunol, 16:83 (1996)). Antibodies to CD40 therefore have the potential to be highly effective therapeutic agents—antagonistic anti-CD40 antibodies can be used as immunosuppressive/anti-inflammatories, while agonistic anti-CD40 antibodies can be used as immunostimulants to boost immune responses in, for example, individuals with compromised immune systems. Several anti-CD40 antibodies are currently in development which are murine, chimeric or humanized. However, non-human or humanized antibodies are limited in their effectiveness because of the development of immune responses to the non-human portions. The invention addresses this problem and provides related advantages.

SUMMARY

Isolated human anti-CD40 antibodies and fragments (e.g., scFv, Fab, Fab', or F(ab')$_2$) thereof that specifically bind to CD40 (e.g., human CD40) and that modulate one or more activities of CD40 are provided. The antibodies may be polyclonal or monoclonal. Specific embodiments include antibodies denoted as no. 11 and 72, and hybridomas denoted as F1-102, F5-152, F2-103, F5-77, F5-157 and F4-465. Specific fragments therefore include fragments of the antibodies denoted as no. 11 and 72, or the antibodies produced by the hybridomas denoted as F1-102, F5-152, F2-103, F5-77, F5-157 and F4-465. Specific light and heavy chains of a human CD40 antibody or fragments therefore are set forth in of SEQ ID NOs:10, 11, 12, 13, 14 and 15.

Additional embodiments include antibodies having the CD40 binding specificity of the antibody denoted as no. 11 or 72, or the antibody produced by the hybridomas denoted as F1-102, F5-152, F2-103, F5-77, F5-157 or F4-465, Yet additional embodiment include antibodies having the CD40 modulating activity of the antibody denoted as no. 11 or 72, or the antibody produced by the hybridoma denoted as F1-102, F5-152, F2-103, F5-77, F5-157 or F4-465.

CD40 activities modulated (i.e., increased or decreased) by a human CD40 antibody include, for example, a CD40 signaling activity. Particular activities include modulation of cell proliferation (e.g., B-cells) or protein expression (e.g., CD95, CD80 or CD86). Human CD40 antibodies include antibodies that decrease or increase binding of a CD40 ligand (e.g., CD40L) to CD40. Human CD40 antibodies may modulate a CD40 activity in the presence or absence of a CD40 ligand, such as CD40L.

Human CD40 antibodies including antibodies comprising a lambda or kappa light chain sequence or a heavy chain sequence are also provided.

Human CD40 antibodies include modified forms such as amino acid substitutions, additions or deletions, as well as containing heterologous functional domains and distinct molecular entities conferring a complementary or distinct functionality on the human CD40 antibodies. Detectably labeled CD40 antibodies are therefore also provided.

Pharmaceutical formulations including human CD40 antibodies are provided. Host cells (e.g. hybridomas) that express human CD40 antibodies are provided. Nucleic acid that encoding human CD40 antibodies as well as host cells containing the nucleic acid encoding human CD40 antibodies are also provided.

Methods of producing human CD40 antibodies that modulate an activity of CD40 are provided. A method includes, for example, administering CD40 or an immunogenic fragment thereof to an animal (e.g. mouse) capable of expressing human immunoglobulin; screening the administered animal for expression of a human CD40 antibody; selecting an animal that produces a human CD40 antibody; isolating an antibody from the animal that produces a human CD40 antibody; and determining whether the human CD40 antibody modulates an activity of CD40 thereby producing a human CD40 antibody that modulates an activity of CD40.

Methods of producing human monoclonal CD40 antibodies that modulate an activity of CD40 are also provided. A method includes, for example, administering human CD40 or an immunogenic fragment thereof to an animal (e.g. mouse) capable of expressing human immunoglobulin; isolating spleen cells from the animal that produces a human CD40 antibody; fusing the spleen cells with a myeloma cell to produce a hybridoma; and screening the hybridoma for expression of a human CD40 antibody that modulates an activity of CD40 thereby producing a human monoclonal CD40 antibody that modulates an activity of CD40.

Antibodies produced by the methods, including monoclonal antibodies isolated from a hybridoma produced by the methods of the invention, are also provided.

Methods for modulating a CD40 signaling activity comprising contacting a cell that expresses CD40 with a modulating amount of a human CD40 antibody are provided. CD40 signaling activities modulated include, for example, increasing or decreasing cell proliferation (e.g., B-cells) or protein expression (e.g., CD95, CD80 or CD86). Methods optionally include the addition of a CD40 ligand, such as CD40L. Embodiments include wherein the CD40 in the cell is human.

In additional embodiments, methods are practiced with an antibody having the binding specificity, a CD40 modulating activity or a CD40 binding affinity of the antibody denoted as no. 11 or 72, or the antibody produced by the hybridoma denoted as F1-102, F5-152, F2-103, F5-77, F5-157 or F4-465.

Methods can be practiced in a subject (e.g., human) in order to modulate one or more CD40 activities in the subject. Methods of increasing and methods for decreasing a CD40 signaling activity in a subject are therefore also provided. In one embodiment, a method includes administering to the subject an amount of a human anti-CD40 antibody that increases a CD40 signaling activity. In another embodiment, a method includes administering to the subject an amount of a human anti-CD40 antibody that decreases a CD40 signaling activity.

Methods can be practiced in a subject (e.g., human) in order to ameliorate a disorder or treat a condition associated with a CD40 activity. That is, a disorder or condition that is likely to respond (e.g., symptoms associated with the disorder or condition are reduced, subject improves, etc.) to increasing or decreasing a CD40 activity can be treated with a human CD40 antibody. Methods for treating a disorder or condition of a subject are therefore also provided. In one embodiment, the condition comprises an immune disorder or an undesirable immune response in a subject, and a method includes administering to the subject an amount of a human anti-CD40 antibody that decreases a CD40 activity thereby ameliorating the immune disorder or inhibiting the undesirable immune response. In another embodiment, the condition comprises an immune disorder in a subject and a method includes administering to the subject an amount of a human anti-CD40 antibody that increases a CD40 activity thereby ameliorating the immune disorder.

Specific immune disorders and undesirable immune responses treatable with the human CD40 antibodies of the invention include, for example, host rejection of a transplanted cell, tissue or organ, inflammation, autoimmunity, a lymphoma, a leukemia or a myeloma. Additional immune disorders include, for example, immunodeficiency, a cell proliferative disorder (e.g., benign hyperplasia or a cancer/tumor).

Additional methods include inducing or stimulating an immune response in a subject. In one embodiment, a method includes administering to the subject an amount of a human anti-CD40 antibody that increases a CD40 activity thereby inducing or stimulating an immune response. Particular immune responses which can be stimulated with a human CD40 antibody include, for example, an immune response against a cell proliferative disorder (e.g., benign hyperplasia or a cancer/tumor) or an infection by a pathogen.

Treatment methods include prophylactic treatment with a human CD40 antibody. Target subjects of such prophylactic treatment methods include subjects at risk of a disorder or subjects that exhibit few if any symptoms associated with a particular disorder, but are susceptible to the disorder.

Methods of detecting the presence of CD40 in a sample or cell are also provided. A method includes, for example, contacting a sample having or suspected of having CD40, or a cell expressing or suspected of expressing CD40, with a human CD40 antibody and detecting the presence of CD40 in the sample or cell. Samples which can be assayed include, for example, a tissue, fluid or other specimen from a subject.

Methods of detecting the presence of a disorder associated with increased or decreased CD40 expression in a subject (e.g., human) are also provided. A method includes, for example, contacting a sample having or suspected of having CD40 or a cell expressing or suspected of expressing CD40, wherein the sample or cell is from or present in the subject (e.g., human), with a human CD40, and detecting the presence of increased or decreased CD40 expression in the sample or cell relative to a control, thereby detecting the presence of a disorder associated with increased or decreased CD40 expression in the subject.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
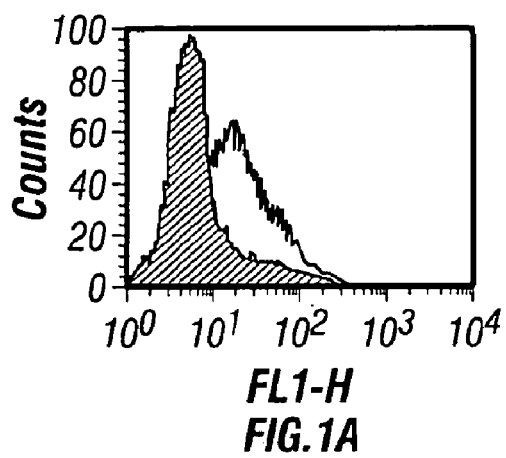
FIG. 1 shows Ramos cell staining activity of (A) anti-human CD40-FITC positive control and anti-human CD40 antibody nos. (B) 11; (C) 366; (D) 72; and (E) 30. Staining activities of antibodies isolated by limiting dilutions were determined as described in Example 1.
Figure 1B:
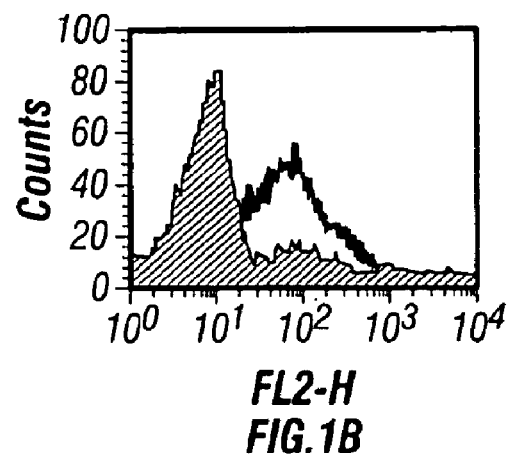
Figure 1C:
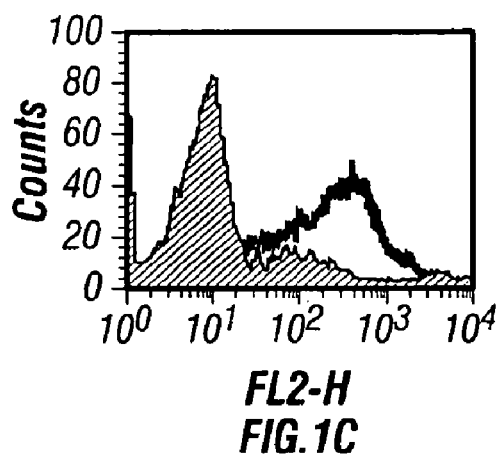
Figure 1D:
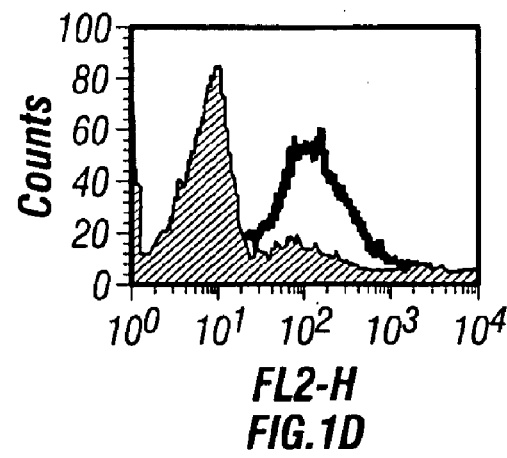
Figure 1E:
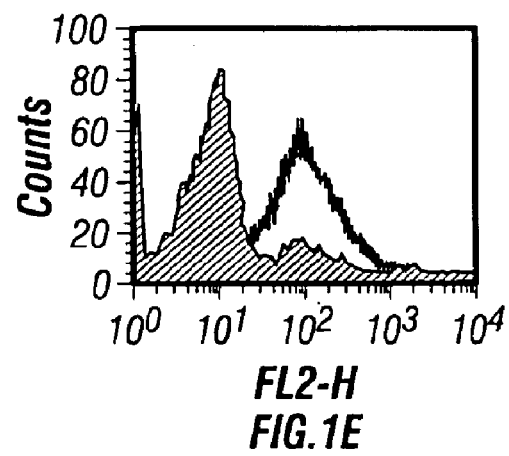

The invention is based, at least in part, on the generation of human antibodies against CD40. That is, the CD40 antibodies of the invention are human immunoglobulin (Ig) amino acid sequences. This means that the invention antibodies are unlikely to elicit any immune response against them when they are introduced into human subjects. The invention CD40 antibodies are therefore less likely to produce hypersensitivity from repeated administration and are more likely to remain in a human subjects' body for a longer period of time due to the absence of a strong immune response.

The invention is also based, at least in part, on the generation of human antibodies against human CD40 that modulate one or more activities of CD40. For example, invention antibodies include CD40 antibodies that inhibit a CD40 activity by decreasing CD40L-induced CD95 expression in Ramos B cells (e.g., nos. 30, 72 and 366, as well as F4-465). Invention antibodies also include CD40 antibodies that inhibit a CD40 activity by decreasing CD40L-induced cell proliferation. Invention antibodies additionally include CD40 antibodies that stimulate a CD40 activity by increasing CD40L-induced CD95 expression in Ramos B cells (e.g., no. 11 and antibodies produced by hybridomas F1-102, F2-103, F5-77, F5-152) or cell proliferation (no. 11). Invention antibodies further include CD40 antibodies having a heavy or light chain of a sequence set forth in SEQ ID Nos:10, 11, 12, 13, 14 or 15.

Thus, in accordance with the invention, there are provided human CD40 antibodies that bind to CD40 (e.g., human CD40). In one embodiment, a CD40 antibody modulates one or more activities of CD40 (e.g., a signaling activity). In one aspect, a CD40 antibody of the invention decreases a CD40 activity (e.g., CD40L induced CD95 expression is reduced or blocked or cell proliferation is inhibited). In another aspect, a CD40 antibody of the invention increases a CD40 activity (e.g., CD40L induced CD95 expression is increased or stimulated or cell proliferation is increased or stimulated).

As used herein, the terms "CD40 antibody" or "anti-CD40 antibody" means an antibody that specifically binds to CD40. "Human CD40 antibody" or "human anti-CD40 antibody" mean that the antibody that specifically binds to CD40 consists of human immunoglobulin amino acid sequences. A human CD40 antibody that binds human CD40 is an antibody comprising human imniunoglobulin amino acid sequences which specifically binds to human CD40, although the antibody may also bind to a non-human sequence that has an epitope that the human CD40 antibody recognizes.

CD40 antibodies of the invention include polyclonal or monoclonal antibodies, as well as fragments and modified forms as sef forth herein. Pooled polyclonal and monoclonal antibodies containing two or more different CD40 antibodies with different binding specificity, binding affinity or functions are also provided.

CD40 antibodies of the invention contain kappa or lambda chain sequences. Each antibody molecule contains two kappa or two lambda light chains. The primary difference between kappa and lambda light chains is in the sequences of the constant region. In humans, the kappa chain variable region sequences have more diversity than lambda chain variable region sequences which results in the generation of more different (diverse) antibodies. Exemplary CD40 antibody produced by hybridoma F4-465 contains a human lambda light chain.

Exemplary antibodies are denoted as nos. 11 (ATCC PTA-2308), 30,72 (ATCC PTA-2309) and 366 or are produced by the hybridomas denoted as F1-102 (ATCC PTA-3337), F2-103, F5-77, F5-152, F5-157, and F4-465 (ATCC PTA-3338). Although not wishing to be bound by theory, exemplary CD40 antibodies that inhibit a CD40 activity, e.g., nos. 30, 72, 366 and antibody produced by hybridoma F4-465 appear to decrease binding of CD40L to CD40 and do not induce CD40 signaling. In contrast, CD40 antibodies that stimulate a CD40 activity, e.g., no. 11 and antibodies produced by hybridomas F1-102, F2-103, F5-77, F5-152 and F5-157, appear to induce CD40 signaling and to enhance CD40L activity.

As used herein, "modulate," when used as a modifier of a term, means that one or activities or functions of the modified term is increased or decreased. Thus, to modulate a CD40 activity means to increase or decrease one or more activities or functions of CD40. Activities of CD40 include intracellular signaling conveyed by CD40 as well as any downstream effect of CD40 signaling which include changes in gene or protein expression (e.g., CD95, CD80 or CD86) or a given cell response such as induction of cell proliferation, isotype switching or development of a condition or disorder in which CD40 participates or plays a role. Exemplary CD40 activities therefore include modulating protein expression or cell proliferation.

Additional examples of CD40 activities include modulating cell survival (e.g., functions as cell survival signal), antibody production, antibody isotype switching, production of cytokines (e.g., IL-2, IL-6, IL-8, IL-12, TNF-α, IL-4, IL-5 and IL-10), metalloproteases (e.g., MMP-I/collagenase and MMP-9/gelatinase B) and establishment of immune memory. CD40 activities further include modulating production of proteins involved in cell-cell contact or adhesion (e.g., E-selectin, VCAM-1 and ICAM-1).

Physiological conditions or disorders in which CD40 signaling participates or which respond to altering one or more CD40 activities (e.g., decreasing a CD40 activity) and are therefore considered to be a CD40 activity include undesirable immune response in vivo, such as autoimmunity, hypersensitivity, inflammation or transplant rejection. Specific examples of autoimmunity include rheumatoid arthritis, lupus (e.g., SLE, lupus nephritis), auto-antibody production, allergies and Crohn's disease. Hypersensitivity treatable by modulating CD40 activity include allergic reactions to antigens, antibiotics, etc. Additional examples of CD40 activities include transplant rejection or an excess immune response to an grafted antigen (e.g., expressed by a transplanted organ), and associated hemodynamic abnormalities such as leukopenia, infiltration of transplanted organ/tissue with T-cells or B-cells and opportunistic infections, inflammation or IgE class switching. Yet additional examples include production of neutralizing antibodies against therapeutic agents or virus vectors for gene therapy. Another example is thrombus formation, artherosclerosis or vessel intimal thickening in a subject.

Examples where increasing a CD40 activity can result in a physiological effect include stimulating an immune response to an infectious agent (e.g., a poorly immunogenic pathogen) or a cancer, or increasing the ability to respond to an antigen by improving memory of cell mediated immunity or humoral immunity. Stimulating cell survival or proliferation of immune cells by stimulating CD40 can also result in treatment.

Invention CD40 antibodies include antibodies having the binding specificity of the CD40 antibodies exemplified herein. Thus, in another embodiment, the invention provides CD40 antibodies having the binding specificity of the antibodies denoted as nos. 11, 30, 72 and 366, and the antibodies produced by the hybridomas denoted as F1-102, F5-152, F2-103, F5-77, F5-157 and F4-465. In one aspect, a CD40 antibody has a heavy or liglit chain sequence as set forth in SEQ ID NOs:10 (ATCC PTA-3302), 11 (ATCC PTA-3303), 12 (ATCC PTA-3306), 13 (ATCC PTA-3307), 14 (ATCC PTA-3304) or 15 (ATCC PTA-3305).

As used herein, the term "binding specificity," when used in reference to an antibody means that the antibody recognizes the same antigenic epitope as a comparison antibody. Thus, a CD40 antibody having the binding specificity of the antibody denoted as no. 11 recognizes the same epitope as the CD40 antibody denoted as no. 11; a CD40 antibody having the binding specificity of the antibody denoted as no. 72 recognizes the same epitope as the CD40 antibody denoted as no. 72; a CD40 antibody having the binding specificity of the antibody produced by the hybridoma denoted as F1-102 recognizes the same epitope as the antibody produced by the hybridoma denoted as F1-102; and so on and so forth.

Typically epitopes are short amino acid sequences, e.g. about five amino acids in length. Systematic techniques for identifying epitopes are known in the art and are described, for example, in U.S. Pat. No. 4,708,871. Briefly, a set of overlapping oligopeptides derived from the CD40 antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to an anti-CD40 nionoclonal antibody. Alternatively, phage display peptide library kits (New England BioLabs) are currently commercially available for epitope mapping. Using these methods, the binding affinity for every possible subset of consecutive amino acids may be determined in order to identify the epitope that a given antibody binds. Epitopes may also be identified by inference when epitope length peptide sequences are used to immunize animals from which antibodies are obtained.

Invention human CD40 antibodies include antibodies having one or more functions of the CD40 antibodies exemplified herein (e.g., a CD40 modulating activity). Thus, in additional embodiments the invention provides CD40 antibodies having one or more functions (e.g., increase or decrease an activity associated with CD40 such as CD95, CD80 or CD86 expression or cell proliferation) of the antibodies denoted as nos. 11, 30, 72 and 366, and the antibodies produced by the hybridomas denoted as F1-102, F5-152, F2-103, F5-77, F5-157 and F4-465.

As used herein, the term "function," when used in comparing an antibody to a reference antibody, means that the antibody has at least one function or activity that is substantially the same as the reference antibody. Thus, a CD40 antibody having a function of the antibody denoted as no. 11 has at least one function or activity that is substantially the same as the CD40 antibody denoted as no. 11; a CD40 antibody having the function of the antibody denoted as no. 72 has at least one function or activity that is substantially the same as the CD40 antibody denoted as no. 72; a CD40 antibody having the function of the antibody produced by the hybridoma denoted as F1-102 has at least one function or activity that is substantially the same as the antibody produced by the hybridoma denoted as F1-102; and so on and so forth.

The term "substantially the same," when used to compare a function or activity of one antibody to another means that the antibody has at least all or a part of one function or activity of the comparison antibody, even though the degree of the function or activity may be different. For example, the CD40 antibody denoted as no. 11 can increase B-cell proliferation when co-incubated with CD40L (see, e.g., Example 3). Thus, a CD40 antibody having a function of the antibody denoted as no. 11 will also stimulate B-cell proliferation, although the degree to which cell proliferation is stimulated by the antibody may be greater or less than no. 11 at the same antibody concentrations. Similarly, the CD40 antibody produced by the hybridoma denoted as F1-102 stimulates CD95 expression on Ramos cells and stimulates B-cell proliferation. Thus, a CD40 antibody having a function of the antibody produced by the hybridoma denoted as F1-102 will either stimulate CD95 expression or B-cell proliferation, although the degree to which CD95 expression or B-cell proliferation is stimulated may be greater or less than antibody produced by the hybridoma denoted as F1-102 at the same antibody concentrations.

Antibodies having a requisite function or activity of exemplified human CD40 antibodies can be identified using the Ramos B cell assays, cell proliferation assays as set forth in Examples 1, 3 and 4, or other CD40 activity assays known in the art. For example, cell proliferation can also be assayed using a Burkitt lymphoma cell line. Examples of Burkitt lymphoma cell lines include Raji (ATCC CCL 86), Daudi (ATCC CCL 213) and Namalwa (ATCC CRL 1432). Another assay for measuring CD40 activity is to measure immunoglobulin produced by B cells in response to activation by CD40L in the presence and absence of a particular CD40 antibody. Immunoglobulin secretion can be measured by incubating cells in culture for a period of time. Immunoglobulin production can be measured by an ELISA assay as described herein or in the art (see, e.g., Maliszewski et al., J. Immunol. 144:3028 (1990)). CD40 stimulatory or inhibitory antibodies can be identified by measuring IL-4 induced IgE secretion of mixed lymphocytes. CD40 signaling also increases expression of co-stimulatory molecules such as CD80 or CD86, or adhesion molecules such as ICAM-1 or LFA-1, or apoptosis-related molecules like CD95 (see, e.g., Durie et al., Immunol. Today, 9:406 (1994)). Altered expression of these molecules can be detected by FACS staining.

Invention CD40 antibodies also include antibodies having substantially the same binding affinity as the CD40 antibodies exemplified herein. Thus, in additional embodiments the invention provides CD40 antibodies having substantially the same binding affinity as the antibodies denoted as nos. 11, 30, 72 and 366, and the antibodies produced by the hybridomas denoted as F1-102, F5-152, F2-103, F5-77, F5-157 and F4-465. In one aspect, a CD40 antibody has a heavy or light chain sequence as set forth in SEQ ID NOs:10, 11, 12, 13, 14 or 15.

The term "substantially the same," when used in reference to antibody binding affinity, means that the dissociation constant ($K_D$) is within about 10–100 fold of the reference antibody. For example, anti-CD40 antibody no. 30, as determined by BiaCore analysis, has a $K_D$ value was 0.8–4 nM. Thus, an antibody having substantially the same binding affinity as anti-CD40 antibody no. 30 would have a $K_D$ value of about 0.008–400 nM.

Invention CD40 antibodies further include antibodies that modulate a CD40 activity in the presence or absence of a CD40 ligand, such as CD40L. Thus, the invention provides CD40 antibodies that modulate a CD40 activity in the presence or absence of a CD40 ligand, such as CD40L. In one embodiment, a CD40 antibody modulates a CD40 activity in the presence of CD40L. In another embodiment, a CD40 antibody modulates a CD40 activity in the absence of CD40L. In one aspect, a CD40 antibody stimulates an activity of CD40 in the presence of CD40L, to a greater extent than in the absence of the CD40 antibody. In another aspect, a CD40 antibody decreases an activity of CD40 in the presence of CD40L.

As used herein, the term "CD40 ligand" means a genus of molecules that are capable of binding CD40 and modulating one or more activities of CD40. A specific example of a CD40 ligand is polypeptide CD40L, CD40L peptide subsequences such as soluble CD40L polypeptides lacking transmembrane or intracellular regions, mammalian homologs of human CD40L (e.g., murine CD40L), structural or functional analogs of mammalian CD40L or derivatives of mammalian CD40L (e.g., peptide subsequences of full length CD40L). Specific CD40L sequences are described, for example, in Spriggs et al., J. Exp. Med. 176:1543 (1992) and Armitage et al., Nature 357:80 (1992). Additional examples of CD40 ligands include drugs that bind to and modulate one or more activities of CD40.

In order to produce human CD40 antibodies, a human CD40 fusion protein (hCD40:hFc) was generated consisting of the extracellular domain of human CD40 fused to the Fc region of human IgG1. The fusion protein was expressed in a baculovirus expression construct and isolated from infected Tn5 insect cells. The CD40 fusion protein was purified with a protein G affinity column and subsequently used to immunize human transchromosomic (Tc) mice, which contain kappa or lambda human IgG chains in their chromosomes (Tomizuka K et al., Proc. Natl. Acad. Sci. USA 97:722 (2000) and Tomizuka K., et al., Nat Genet 16:133 (1997)). Mice showing highest antibody titers were used for cell fusions. Monoclonal antibodies were then prepared from the animals using a modified method of Kohler and Milstein, Nature 256:495 (1975). The spleen was removed and dissociated into single cells which were then fused with myeloma cells to form hybridomas. The resulting hybridomas were plated and assayed for the production of heavy or kappa chains and then for CD40 antibody production. Cells were then cloned by limiting dilution and rescreened for aCD40 antibody production.

The selected secreting hybridomas are then cultured either in vitro (e.g., in tissue culture), or in vivo (as ascites in mice)

and human CD40 antibodies purified. The antibodies were purified with a commercially available protein G affinity resin. Antibodies may also be isolated or purified by other techniques well known in the art (see *Antibodies: A Laboratory Manual*, Harlow and Lane (eds.), Cold Spring Harbor Laboratory Press, 1988). Suitable techniques include CD40 affinity purification, non-denaturing gel purification, HPLC or RP-HPLC, purification on protein A column, or any combination of these techniques. The purified antibodies are determined to be human Ig by using mouse Ig-absorbed anti-human Ig in an ELISA assay.

CD40 protein suitable for generating antibodies can be produced by any of a variety of standard protein purification or recombinant expression techniques known in the art. For example, as exemplified herein the CD40 peptides may be expressed in a cell and protein produced by the cells may be purified. CD40 protein may be expressed as a part of a larger protein by recombinant methods. Alternatively, CD40 antigen can be produced by standard peptide synthesis techniques, such as solid-phase synthesis. A portion of the protein may contain an amino acid sequence such as a T7 tag or polyhistidine sequence to facilitate purification of expressed or synthesized CD40.

Forms of CD40 suitable for generating an immune response against CD40 include soluble forms of CD40, or peptide subsequences of full length CD40 (e.g., typically five amino acids or more in length). Additional forms of CD40 include CD40 containing preparations or extracts, partially purified forms of CD40 as well as cells CD40 or viruses that express CD40 or preparations of such cells or viruses.

Monoclonal antibodies may also be readily generated using other techniques (see U.S. Pat. Nos. 4,902,614, 4,543,439, and 4,411,993; see also *Monoclonal Antibodies Hybridomas: A New Dimension in Biological Analyses*, Plenum Press, Kennett, McKearn, and Bechtol (eds.), 1980, and Harlow et al. (1988), supra). The preparation of polyclonal antibodies and their purification also is well known to those skilled in the art (see, e.g., Green et al. (1992) In: *Immunochemical Protocols*, pages 1–5, Manson, ed., Humana Press; Harlow et al. (1988), supra; and Coligan et al. (1994) In: *Current Protocols in Immunology*, Wiley; and Barnes et al. (1992) In: *Methods in Molecular Biology*, Vol. 10, pages 79–104, Humana Press).

Animals which may be immunized include rabbits, rats, sheep goats, or guinea pigs; such animals may be modified to include human IgG gene loci. Additionally, many techniques are known in the art for increasing the immune response, for example by coupling the soluble CD40 to another protein such as ovalbumin or keyhole limpet hemocyanin (KLH), thyroglobulin and tetanus toxoid, or through the use of adjuvants such as Freund's complete or incomplete adjuvant. The initial and any optional subsequent immunization may be through intraperitoneal, intramuscular, intraocular, or subcutaneous routes. Subsequent immunizations may be at the same or at different concentrations of antigen preparation, and may be at regular or irregular intervals.

Thus, in another embodiment, the invention provides methods of producing human CD40 antibodies (polyclonal and monoclonal) including antibodies that modulate an activity of CD40. In one embodiment, a method includes administering CD40 or an immunogenic fragment thereof to an animal (e.g., a mouse) capable of expressing human immunoglobulin; screening the animal for expression of human CD40 antibody; selecting an animal that produces a human CD40 antibody; isolating an antibody from the animal that produces human CD40 antibody; and determining whether the human CD40 antibody modulates an activity of CD40 thereby identifying a human CD40 antibody that modulates an activity of CD40. In another embodiment, a method includes administering human CD40 or an immunogenic fragment thereof to an animal (e.g., a mouse) capable of expressing human immunoglobulin; isolating spleen cells from the mouse that produces human CD40 antibody; fusing the spleen cells with a myeloma cell to produce a hybridoma; and screening the hybridoma for expression of a human CD40 antibody that modulates an activity of CD40 thereby identifying a hybridoma that produces a human CD40 antibody.

The invention further provides human CD40 antibodies that have been modified. Examples of modifications include one or more amino acid substitutions, additions or deletions of CD40 antibody which have all or at least part of a function of unmodified CD40. Modified human CD40 antibody should be relatively non-immunogenic in a human subject, that is, the antibody does not elicit a strong immune response in a human subject. In particular embodiments, human CD40 antibody fragments comprise an scFv, Fab, Fab', or F(ab')$_2$ fragment. In particular aspects, the scFv, Fab, Fab', or F(ab')$_2$ fragments have substantially the same binding specificity, at least one activity of full length human CD40 antibody or substantially the same binding affinity of unmodified CD40 antibody. In more particular aspects, antibody fragments are scFv, Fab, Fab', or F(ab')$_2$ fragments of the antibodies denoted as nos. 11, 30, 72 and 366, and the antibodies produced by the hybridoma denoted as F1-102, F5-152, F2-103, F5-77, F5-157 and F4-465. In additional embodiments, human CD40 antibody having one or more amino acid substitutions, additions or deletions has substantially the same binding specificity, at least one activity of unmodified human CD40 antibody or substantially the same binding affinity of unmodified human CD40 antibody. In specific aspects, modified forms are of a heavy or light chain sequence set forth in SEQ ID NOs:10, 11, 12, 13, 14 or 15.

CD40 antibody fragments (e.g., Fab, Fab', F(ab')2, and scFv) of the invention can be prepared by proteolytic hydrolysis of the antibody, for example, by pepsin or papain digestion of whole antibodies. In particular, antibody fragments produced by enzymatic cleavage with pepsin provide a 5S fragment denoted F(ab')$_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., Goldenberg, U.S. Pat. Nos. 4,036,945 and 4,331,647 and references cited therein; Edelman et al. Methods in Enymology 1:422 (1967); and Coligan et al., at sections 2.8.1–2.8.10 and 2.10.1–2.10.4, supra). Other methods of cleaving antibodies, such as separation of heavy chains to form monovalent light-heavy chain fragments, further cleavage of fragments, or other enzymatic or chemical may also be used. Genetic techniques include expression of all or a part of the CD40 antibody gene into a host cell such as Cos cells or *E. coli*. The recombinant host cells synthesize intact or single antibody chain, such as a scFV (see, e.g., Whitlow et al., In: *Methods: A Companion to Methods in Enzymology* 2:97 (1991), Bird et al., Science 242:423 (1988); and U.S. Pat. No. 4,946,778).

Substitutions may be conservative or non-conservative and may be in the constant or variable regions of the antibody. One or a few conservative amino acid substitutions in constant or variable regions are likely to be tolerated. Particular examples of conservative amino acid substitutions are Ile, Val, Leu or Ala for one another; Lys and Arg for one another; Glu and Asp for one another; and Gln and Asn for one another. Non-conservative substitution of multiple amino acids in hypervariable regions is likely to affect binding activity, specificity or antibody function or activity. Thus, substitutions in a hypervariable region may be assayed for their effect in order to identify those retaining at least a part of the binding activity, specificity or antibody function or activity of unsubstituted antibody. Such antibodies having amino acid substitutions are included so long as at least a part of binding specificity, one activity or binding affinity of unmodified human CD40 antibody is retained by the substituted antibody relative to unsubstituted antibody.

Another particular example of a modified CD40 antibody having an amino acid addition is one in which a second heterologous sequence, i.e., heterologous functional domain, that confers a distinct or complementary function on the antibody. For example, an amino acid tag such as T7 or polyhistidine can be attached to the antibody in order to facilitate purification or detection. Yet another particular example is addition of a peptide toxin such as botulinum toxin attached to a CD40 antibody in order to target cells which express CD40 for killing. Thus, in other embodiments the invention provides chimeric CD40 antibodies wherein a CD40 antibody has one or more amino acids conferring a distinct function, i.e. a heterologous functional domain, on the antibody.

Heterologous functional domains are not restricted to amino acid sequences. Thus, a heterologous functional domain can consist of any of a variety of different types of small or large functional moieties. Such moieties include nucleic acid, peptide, carbohydrate, lipid or small organic compounds, such as a drug (e.g., a chemothrerapeutic drug such as vincristine, methotrexate, etc.)

Linker sequences may be inserted between the antibody sequence and the heterologous functional domain so that the two maintain, at least in part, their function or activity. Linker sequences may have one or more properties that include a flexible conformation, an inability to form an ordered secondary structure or a hydrophobic or charged character which could promote or interact with either functional domain. Amino acids typically found in flexible protein regions include Gly, Asn and Ser which is expected to satisfy the above criteria for a linker sequence. Other near neutral amino acids, such as Thr and Ala, may also be used in the linker sequence. The length of the linker sequence may vary without significantly affecting a function or activity of the fusion protein (see, e.g., U.S. Pat. No. 6,087,329).

Additional examples of antibody modifications are detectable labels. Thus, in another embodiment, the invention provides human CD40 antibodies that are detectably labeled.

Specific examples of labels include fluorophores, chromophores, radioactive isotopes (e.g., $I^{125}$), electron-dense reagents, enzymes and ligands. Enzymes are typically detected by their activity. For example, horseradish peroxidase is usually detected by its ability to convert a substrate such as 3,3',5,5'-tetramethylbenzidine (TMB) to a blue pigment, which can be quantified. Ligands may bind other molecules such as biotin, which may bind avidin or streptavidin, IgG which may bind protein A, and the numerous receptor-ligand complexes known in the art. It is understood that a CD40 antibody may have two or more modifications or labels. For example, a monoclonal antibody may be coupled to biotin to detect its presence with avidin as well as labeled with $I^{125}$ so that it provides a signal. Other permutations and possibilities will be readily apparent to those of ordinary skill in the art, and are considered as within the scope of the invention.

The invention further provides nucleic acids encoding the human CD40 antibodies of the invention, including modified forms, fragments, chimeras, etc. In particular embodiments, a nucleic acid encodes intact or single chain CD40 antibody denoted as no. 11, 30, 72 and 366, or an antibody produced by hybridomas denoted as F1-102, F5-152, F2-103, F5-77, F5-157 and F4-465. In particular aspects, the nucleic acid comprises SEQ ID NOs:10, 11, 12, 13, 14 or 15. In additional aspects, anucleic acid encodes a subsequence of intact or single chain antibody denoted as no. 11, 30, 72 and 366, or an antibody produced by hybridomas denoted as F1-102, F5-152, F2-103, F5-77, F5-157 and F4-465, e.g., a subsequence of SEQ ID NOs:10, 11, 12, 13, 14 or 15.

The terms "nucleic acid" or "polynucleotide" are used interchangeably to refer to all forms of nucleic acid, including deoxyribonucleic acid (DNA) and ribonucleic acid (RNA). The nucleic acids can be double, single strand, or triplex, linear or circular. Nucleic acids include genomic DNA, cDNA, and antisense. RNA nucleic acid can be spliced or unspliced mRNA, rRNA, tRNA or antisense (e.g., RNAi). Nucleic acids of the invention include naturally occurring, synthetic, as well as nucleotide analogues and derivatives. Such altered or modified polynucleotides include analogues that provide nuclease resistance, for example. Nucleic acid can be of any length, e.g., any of SEQ ID NOs:10, 11, 12, 13, 14 or 15. Nucleic acid lengths also can be less than exemplified SEQ ID NOs:10, 11, 12, 13, 14 or 15. For example, a subsequence of any of SEQ ID NOs: 10, 11, 12, 13, 14 or 15 can encode a CD40 antibody heavy or light chain or kappa or lambda chain fragment that has at least part of the binding specificity, binding affinity or function of full length SEQ ID NOs:10, 11, 12, 13, 14 or 15.

As a result of the degeneracy of the genetic code, the nucleic acids include sequences that are degenerate with respect to a sequence set forth in SEQ ID NOs:10, 11, 12, 13, 14 and 15. Thus, the invention includes nucleic acid having nucleotide alterations from a sequence set forth in SEQ ID NOs:10, 11, 12, 13, 14 or 15, which still encode intact or single chain CD40 antibody, or subsequences thereof.

Nucleic acid can be produced using any of a variety of well known standard cloning and chemical synthesis methods and can be altered intentionally by site-directed mutagenesis or other recombinant techniques known to those skilled in the art. Purity of polynucleotides can be determined through sequencing, gel electrophoresis and the like.

The nucleic acids of the invention may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element operatively linked to a nucleic acid sequence controls transcription and, as appropriate, translation of the nucleic acid sequence. An expression control element can include, as appropriate, promoters, enhancers, transcription terminators, gene silencers, a start codon (e.g., ATG) in front of a protein-encoding gene, etc.

The term "operatively linked" refers to a juxtaposition wherein the components so described are in a relationship permitting them to function in their intended manner. Typically such elements are juxtaposed at the 5' or the 3' ends of the genes but can also be intronic. A particular example is a nucleic acid encoding a CD40 antibody operatively linked to an expression control element such that expression of the nucleic acid is under the control of the element.

Expression control elements include elements that activate transcription constituitively, that are inducible (i.e., require an external signal for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" is meant a minimal sequence element sufficient to direct transcription.

The nucleic acids of the invention may be inserted into a plasmid for propagation into a host cell and for subsequent genetic manipulation if desired. A plasmid is a nucleic acid that can be stably propagated in a host cell, plasmids may optionally contain expression control elements in order to drive expression of the nucleic acid encoding CD40 antibody in the host cell. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of CD40 antibody encoding nucleic acids, producing CD40 antibodies or antisense, and expressing the CD40 antibodies in host cells or organisms, for example.

When cloning in bacterial systems, constitutive promoters such as T7 and the like, as well as inducible promoters such as pL of bacteriophage λ, plac, ptrp, ptac (ptrp-lac hybrid promoter) may be used, as well as inducible promoters (e.g., tetracycline responsive). When cloning in insect cell systems, constitutive or inducible promoters (e.g., ecdysone) may be used. When cloning in mammalian cell systems, constitutive promoters such as SV40, RSV and the like, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat) may be used. Vectors based on bovine papilloma virus (BPV) which have the ability to replicate as extrachromosomal elements (Sarver et al., Mol. Cell. Biol. 1:486 (1981)) also may be used. Alternatively, a retroviral genome can be genetically modified for introducing and directing expression of a CD40 antibody in mammalian host cells.

Expression systems further include vectors specifically designed for in vivo use including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO92/05266 and WO92/14829). Bovine papilloma virus (BPV) has also been employed in gene therapy (U.S. Pat. No. 5,719,054). Such gene therapy vectors also include CMV based vectors (U.S. Pat. No. 5,561,063).

In yeast, a number of vectors containing constitutive or inducible promoters may be used (see, e.g., Ausubel et al., In: Current Protocols in Molecular Biology, Vol. 2, Ch. 13, ed., Greene Publish. Assoc. & Wiley Interscience, 1988; Grant et al. Methods in Enzymology, 153:516 (1987), eds. Wu & Grossman; Bitter Methods in Enzymology, 152:673 (1987), eds. Berger & Kimmel, Acad. Press, N.Y.; and, Strathem et al., The Molecular Biology of the Yeast Saccharomyces (1982) eds. Cold Spring Harbor Press, Vols. I and II). A constitutive yeast promoter such as ADH or LEU2 or an inducible promoter such as GAL may be used (R. Rothstein In: DNA Cloning A Practical Approach, Vol. 11, Ch. 3, ed. D. M. Glover, IRL Press, Wash., D.C., 1986). Alternatively, vectors that facilitate integration of foreign nucleic acid sequences into a yeast chromosome, via homologous recombination for example, are known in the art and can be used. Yeast artificial chromosomes (YAC) are typically used when the inserted polynucleotides are too large for more conventional vectors (e.g., greater than about 12 kb).

The invention also provides nucleic acids encoding human CD40 antibodies of the invention inserted into host cells. In one embodiment, the host cell is a prokaryotic cell. In another embodiment, the host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded CD40 expressed. The term also includes any progeny of the subject host cell. Host cells include progeny cells which may not be identical to the parental cell since there may be mutations that occur during replication. Nevertheless, such cells are considered to be host cells of the invention.

Host cells include but are not limited to microorganisms such as bacteria or yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); or animal cell systems infected with recombinant virus expression vectors (e.g., retroviruses, adenovirus, vaccinia virus), or transformed animal cell systems engineered for stable expression, are provided.

The expression vector also can contain a nucleic acid encoding a selectable marker conferring resistance to a selective pressure or identifiable marker (e.g., β-galactosidase), thereby allowing cells having the vector to be identified, grown and expanded. Alternatively, a selectable marker can be on a second vector which is cotransfected into a host cell with a first vector containing an invention polynucleotide.

A number of selection systems may be used, including, but not limited to the herpes simplex virus thymidine kinase gene (Wigler et al., Cell 11:223 (1977)), hypoxanthine-guanine phosphoribosyltransferase gene (Szybalska et al., Proc. Natl. Acad. Sci. USA 48:2026 (1962)), and the adenine phosphoribosyltransferase (Lowy et al., Cell 22:817 (1980)) genes can be employed in tk−, hgprt− or aprt− cells respectively. Additionally, antimetabolite resistance can be used as the basis of selection for dhfr, which confers resistance to methotrexate (O'Hare et al., Proc. Natl. Acad. Sci. USA 78:1527 (1981)); the gpt gene, which confers resistance to mycophenolic acid (Mulligan et al., Proc. Natl. Acad. Sci. USA 78:2072 (1981)); the neomycin gene, which confers resistance to the aminoglycoside G-418 (Colberre-Garapin et al., J. Mol. Biol. 150:1 (1981)); puromycin; and the hygromycin gene, which confers resistance to hygromycin (Santerre et al., Gene 30:147 (1984)). Additional selectable genes include trpB, which allows cells to utilize indole in place of tryptophan; hisD, which allows cells to utilize histinol in place of histidine (Hartman et al., Proc. Natl. Acad. Sci. USA 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory).

As disclosed herein, invention human CD40 antibodies include antibodies capable of modulating one or more activities of CD40. Thus, a CD40 antibody of the invention, including modified forms, fragments and nucleic acids encoding CD40 antibodies, nucleotide variants and subsequences thereof, can be used to modulate one or more activities of CD40 in a cell, tissue, organ or whole organism in vitro, in vivo or ex vivo. For example, where it is desired to decrease a CD40 activity, a CD40 antibody that decreases an activity of CD40 (e.g., nos. 30, 72, 366 and antibody produced by hybridoma F4-465) can be used to decrease CD40 activity. Where it is desired to increase a CD40 activity, a CD40 antibody that increases an activity of CD40 (e.g., no. 11 and antibodies produced by hybridomas F1-102, F2-103, F5-77, F5-152 and F5-157) can be used to increase CD40 activity.

Thus, the invention provides methods of modulating a CD40 activity in a cell, tissue, organ or whole organism in vitro, in vivo or ex vivo. In one embodiment, a method of the invention includes contacting a cell, tissue, organ or whole organism in vitro, in vivo or ex vivo with a modulating amount of a human CD40 antibody. In one aspect, the CD40 modulated is human. In other aspects, a CD40 signaling activity, in the presence or absence of a CD40 ligand (e.g., CD40L), is increased (e.g., as reflected by increased CD95, CD80 or CD86 expression or increased cell proliferation). In yet other aspects, a CD40 signaling activity, in the presence or absence of a CD40 ligand (e.g., CD40L), is decreased (e.g., as reflected by decreased CD95, CD80 or CD86 expression or decreased cell proliferation). In still another aspect, a CD40 antibody has the binding specificity, binding affinity or one or more functions of a CD40 antibody denoted as no. 11, 30, 72 or 366, or an antibody produced by hybridomas denoted as F1-102, F5-152, F2-103, F5-77, F5-157 or F4-465. In particular aspects, the CD40 antibody comprises a CD40 antibody denoted as no. 11, 30, 72 or 366, or an antibody produced by hybridomas denoted as F1-102, F5-152, F2-103, F5-77, F5-157 or F4-465. In more particular aspects, an antibody has a heavy or light chain sequence as set forth in SEQ ID NOs:10, 11, 12, 13, 14 or 15.

CD40 plays a significant role in immune cell function and signaling, including B-cell and T-cell activation by antigen presenting cells, such as macrophages and dendritic cells. CD40 appears to function as a cell survival signal in this context. CD40 activation stimulates antibody production, isotype switching, and establishment of memory. CD40 activation stimulates production of cytokines, such as IL-2, IL-6, IL-8, IL-12, TNF-α, IL-4, IL-S and IL-10; and metalloproteases, such as MMP-I/collagenase and MMP-9/gelatinase B. CD40 activation stimulates production of proteins involved in cell-cell contact or adhesion, such as E-selectin, VCAM-1 and ICAM-1. CD40 recognition on target cells provides an activation pathway for NK cell cytotoxic activity. Thus, increasing or decreasing cell survival, antibody production, isotype switching, establishment of memory, production of cytokines, metalloproteases or proteins involved in cell-cell contact or adhesion, or NK cell cytotoxic activity can all be effected by contacting an appropriate cell with a CD40 antibody of the invention.

Thus, the invention further provides methods of modulating cell survival, antibody production, isotype switching, establishment of memory, production of cytokines, metalloproteases or proteins involved in cell-cell contact or adhesion, or NK cell cytotoxic activity comprising contacting a cell with a modulating amount of a CD40 antibody. Such methods can be practiced on a subject in order to achieve the effect in the subject.

Methods of modulating a CD40 activity can be employed to treat a CD40 associated disorder. The invention therefore also provides methods of treating a CD40 associated disorder. As used herein, the term "CD40 associated disorder" means any undesirable physiological condition or pathological disorder in which modulating a CD40 activity may improve or reduce one or more undesirable symptoms of the condition or disorder.

For example, a human CD40 antibody of the invention that decreases an activity of CD40 can be used to treat a CD40 associated disorder where decreasing the CD40 activity improves or reduces one or more undesirable symptoms of the disorder. Thus, where CD40 is associated with an undesirable immune response or process in vivo, such as autoimmunity, hypersensitivity, inflammation or transplant rejection, an invention CD40 antibody that decreases a CD40 activity can be administered to a subject having, or at risk of having autoimmunity, hypersensitivity, inflammation or transplant rejection in order to inhibit or prevent autoimmunity, hypersensitivity, inflammation or transplant rejection in the subject.

Particular examples of autoimmune disorders treatable with a human CD40 antibody of the invention include rheumatoid arthritis, lupus (e.g., SLE, lupus nephritis), production of auto-antibodies which, in the case of antibodies against myelin basic protein contribute to multiple sclerosis and in the case of antibodies against insulin contribute to diabetes, and Crohn's disease. Hypersensitivity treatable with a CD40 antibody of the invention include allergic reactions to antigens, antibiotics, etc.

Particular examples of inflammation treatable with a human CD40 antibody of the invention include vascular inflammatory disease (e.g., artherosclerotic lesions, plaque disruption and thrombus formation), production of inflammatory cytokines (e.g., LIF, GM-CSF, and IL-6), lung fibrosis and inflammation associated with multiple sclerosis or a tissue or organ transplant. CD40 activity can be associated with inflammation caused by viral myocarditis and, as such, a CD40 antibody that inhibits a CD40 activity can be used to inhibit inflammation associated with viral infection.

Particular examples of transplant rejection (acute or chronic) treatable with a human CD40 antibody of the invention include blood vessels, kidney, liver, heart, lung, pancreas and skin. Transplantation includes grafting of tissues or organ from the body of an individual to a different place within the same or a different individual. Transplantation also involves grafting of tissues or organs from one area of the body to another. Transplantation of tissues or organs between genetically dissimilar animals of the same species is termed as allogeneic transplantation. Transplantation of animal organs into humans is termed xenotransplants.

Thus, human CD40 antibodies of the invention may be used alone or in combination with therapeutic agents that inhibit rejection of a transplanted organ. Examples of such agents are azathioprine, corticosteroids and cyclosporine. A CD40 antibody treatment may also lessen or prevent the side effects frequently observed in transplant recipients who undergo immune suppressive therapy, for example, fever, anorexia, hemodynamic abnormalities, leukopenia, infiltration of transplanted organ/tissue with T-cells or B-cells and opportunistic infections.

Additional situations exist in which it may be desired to inhibit an immune response. For example, production of neutralizing antibodies against therapeutic agents, such as anti-insulin antibodies in diabetics administered insulin repeatedly, or in subjects that produce anti-virus antibodies (e.g., adenovirus or adeno-associated virus) being treated with a gene therapy virus vector, may be inhibited using a CD40 antibody of the invention.

A human CD40 antibody that increases an activity of CD40 can be used to treat a CD40 associated disorder where increasing the CD40 activity improves or reduces one or more undesirable symptoms of the disorder. Thus, a CD40 antibody that increases a CD40 activity can be used to treat a subject in which it is desired to increase or stimulate an immune response. There are many situations in which it would be desirable to stimulate an immune response. For example, in the case of a cancer, a CD40 antibody that stimulates a CD40 activity can be used to potentiate an immune response against the cancer. For an infectious disease, a CD40 antibody that stimulates a CD40 activity can be used to potentiate an immune response against the infection.

CD40 activity is thought to be involved in generation of memory in cell mediated antiviral immunity. Thus, a human CD40 antibody of the invention that stimulates a CD40 activity can be used to promote memory which, in turn, can promote a more rapid immune response against a virus, for example. A CD40 antibody that stimulates a CD40 activity can improve an immune response against poorly immunogenic pathogens, such as *Haemophilus influenzae, Streptococcus pneumoniae* and *Neisseria meningitis*, for example.

CD40 is also present in various other tissues and cells. For example, CD40 is present in epithelial cells, vascular endothelium and smooth muscle cells, and CD40 ligand (CD154) was expressed by thrombin-activated platelets. These findings indicate a role for CD40 activity in vascular thrombotic-atheromatic pathophysiology. Therefore, a human CD40 antibody of the invention that decreases a CD40 activity can be used to inhibit thrombus formation or artherosclerosis in a subject.

CD40 is also expressed in human renal tubules, thymic epithelia and neural cells. Interestingly, CD40 activation appears to induce apoptosis in neural cells, in contrast to its cell survival role in the immune system. Thus, a human CD40 antibody of the invention that decreases a CD40 activity can be used to inhibit apoptosis in neural cells. Accordingly, CD40 can be used to treat neural disorders characterized by cell degeneration or undesirable or excessive cell death, such as Parkinson's disease, Alzheimer's, Huntington disease, spinocerebellar ataxias/atrophies, etc.

CD40 is also expressed in carcinomas, such as melanoma, Kaposi's sarcoma, osteosarcoma and Ewing' sarcoma. CD40 in malignant melanoma appears to be predictive of a negative prognosis. CD40 in human bladder carcinoma cells inhibits fas-mediated apoptosis. CD40 has been detected in tumor vasculature in a renal carcinoma mass. Stimulation of CD40 in B-cell lymphomas stimulates growth. CD40 can therefore function as a cell survival or growth factor in some tumors, and may promote angiogenesis. Other data indicate that CD40 may induce cell death in transformed cells.

Thus, CD40 apparently has dual functions in cancer cells; in some, it promotes survival or cell proliferation/growth, whereas in others it stimulates apoptosis. Thus, a human CD40 antibody of the invention that decreases a CD40 activity associated with tumor survival will be useful in treating cell proliferative disorders (e.g., tumors) in which CD40 functions as a cell survival signal or growth promoter, either directly (e.g., in the tumor cell) or indirectly (i.e., through stimulation of angiogenesis within a tumor mass). A human CD40 antibody of the invention that increases a CD40 activity associated with a decrease in proliferation or an increase in apoptosis will be useful in treating cell proliferative disorders (e.g., tumors) in which CD40 functions as a factor that promotes or stimulates apoptosis, cell death or growth arrest, either directly (e.g., in the tumor cell) or indirectly (e.g., through stimulation of an immune response against the tumor).

Other biological pathways and physiological conditions that CD40 participates in are described in Biancone, et al. (Int. J. Mol. Med. 3:343 (1999)), Laman et al. (Dev. Immunol. 6:215 (1998)), Kooten and Bachereau (J. Leukoc. Biol. 67:2 (2000)), Noelle et al. (Ann. NY Acad. Sci. 815:384 (1997)), Noelle (Immunity 4:415 (1996)), Grewal et al. (Curr. Opin. Immunol. 9:491 (1997)); Grewal et al. (Ann. Rev. Immunol. 16:111 (1998); Grewal et al. (Immunol. Rev. 153:85 (1996)); Gruss et al. (Leuk. Lymphoma 24 (5–6):393 (1997)); van Kooten et al. (Curr. Opin. Immunol. 9:330 (1997)). Such pathways as well as others known in the art are amenable to modulation using the human CD40 antibodies of the invention, as are the physiological conditions associated with CD40 activity described therein or otherwise known in the art.

Of course, human CD40 antibodies of the invention can be used in combination with other therapies that increase or decrease a CD40 activity or that complement CD40 antibody function. For example, a human CD40 antibody of the invention that decreases a CD40 activity may be used with a immunosuppressive drug (e.g., steroids) or another therapeutic protocol for treating autoimmune disorders, inflammation or for inhibiting transplant rejection. Likewise, a human CD40 antibody of the invention that increases a CD40 activity may be used with a immunopotentiating drug or another therapeutic protocol for increasing immune responsiveness to a pathogen or a cancer, or to improve immune memory.

The methods of the invention, including treating a CD40 associated disorder of a subject, likely results in an improvement in the subjects' condition, a reduction of symptoms or decreasing the subject's risk for developing symptoms associated with a CD40 associated disorder. Improvements therefore include one or more decreased symptoms associated with autoimmunity, allergy, graft vs. host disease, etc. An improvement may also be reducing the frequency or amount of a drug used for treating a subject having or at risk of having a CD40 associated disorder. For example, autoimmune patients treated with steroids may require less steroid when treated in combination with a human CD40 antibody. An improvement therefore would include reducing the dosage frequency or amount of steroid that the subject was administered in comparison to the dosage frequency or amount administered prior to treatment with a human CD40 antibody of the invention.

An improvement may be relatively short in duration, e.g., several hours, days or weeks, or extend over a longer period of time, e.g., months or years. The improvement need not be a complete ablation of any or all symptoms of the disorder. For example, reducing severe rheumatoid arthritis to a less severe form is an improvement. Thus, a satisfactory clinical endpoint is achieved when there is an incremental improvement or a partial reduction in the subjects condition or associated symptoms, over a short or long duration.

Target subjects include those having a CD40 associated disorder as described herein or known in the art. Target subjects also include those at risk of developing a CD40 associated disorder. The invention methods are therefore applicable to treating a subject who is at risk of developing a CD40 associated disorder or who has not yet exhibited overt symptoms of the disorder. Prophylactic methods are therefore also included.

At risk subjects appropriate for treatment can be identified as having a genetic predisposition or family history to developing a CD40 associated disorder. At risk subjects can therefore be identified using routine genetic screening for the presence of the genetic lesion or inquiry into the subjects' family history to establish that they are at risk of the disorder. A particular example of an at risk subject would be one with a family history or other genetic characteristic indicating predisposition to a cancer in which the neoplastic or drug-resistant neoplastic cells express CD40. A particular example of a genetic disease is X-linked hyper IgM syndrome, which is known to be caused by a deficient CD40L–CD40 interaction (Allen at al., Science, 259:990 (1993)).

CD40 antibodies can be administered as a single or multiple dose e.g., one time per week for between about 1 to 10 weeks, or for as long as appropriate, for example, to achieve a reduction in the severity of one or more symptoms of a CD40 associated disorder. Doses can vary depending upon the disorder being treated, the extent or severity of the disorder, the clinical endpoint desired, previous or simultaneous treatments, the general health, age, sex or race of the subject and other factors that will be appreciated by the skilled artisan. The skilled artisan will appreciate the factors that may influence the dosage and timing required to provide an amount sufficient for therapeutic benefit. Doses can be empirically determined or determined using animal disease models or optionally in human clinical trials. In the methods of the invention, including prophylactic and therapeutic treatments, the methods doses or protocols may be specifically tailored or modified based on pharmacogenomic data.

The term "subject" refers to animals, typically mammalian animals, such as a non human primate (apes, gibbons, chimpanzees, orangutans, macaques), a domestic animal (dogs and cats), a farm animal (horses, cows, goats, sheep, pigs), experimental animal (mouse, rat, rabbit, guinea pig) and humans. Subjects include animal disease models (e.g., autoimmune mice, such as RA mice, colitis, transplantation and GvHD animals).

The CD40 antibodies of the invention, including modified forms, fragments and nucleic acids encoding CD40 antibodies, nucleotide variants and subsequences thereof, can be incorporated into pharmaceutical compositions. Such pharmaceutical compositions are useful for administration to a subject in vivo or ex vivo, and for providing therapy for a CD40 associated disorder in order to practice the methods of the invention, for example.

Pharmaceutical compositions include "pharmaceutically acceptable" and "physiologically acceptable" carriers, diluents or excipients. As used herein the term "pharmaceutically acceptable" and "physiologically acceptable" includes solvents (aqueous or non-aqueous), solutions, emulsions, dispersion media, coatings, isotonic and absorption promoting or delaying agents, compatible with pharmaceutical administration. Such formulations can be contained in a tablet (coated or uncoated), capsule (hard or soft), microbead, emulsion, powder, granule, crystal, suspension, syrup or elixir. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes.

Pharmaceutical compositions for parenteral, intradermal, or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. In many cases, isotonic agents, for example, sugars, polyalcohols such as manitol, sorbitol, sodium chloride are included in the composition. Including an agent which delays absorption, for example, aluminum monostearate and gelatin can prolonged absorption of injectable compositions.

Sterile injectable solutions can be prepared by incorporating the active compound in the required amount in an appropriate solvent with one or a combination of above ingredients followed by filtered sterilization. Generally, dispersions are prepared by incorporating the active compound into a sterile vehicle containing a basic dispersion medium and other ingredients from those above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. For transdermal administration, the active compounds are formulated into ointments, salves, gels, or creams as generally known in the art.

Biodegradable, biocompatable polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known to those skilled in the art, for example, as described in U.S. Pat. No. 4,522,811.

Antibodies can be chemically modified by covalent conjugation to a polymer to increase their circulating half-life, for example. Particular polymers, and methods to attach them to peptides, are described in U.S. Pat. Nos. 4,766,106; 4,179,337; 4,495,285; and 4,609,546. Examples of polymers are polyoxyethylated polyols and polyethylene glycol (PEG).

Additional pharmaceutical formulations and delivery systems are known in the art and are applicable in the methods and compositions of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky et al., *Drug Delivery Systems*, R. L. Juliano, ed., Oxford, N.Y. (1980), pp. 253–315)

The pharmaceutical formulations can be packaged in unit dosage form for ease of administration and uniformity of dosage. Unit dosage form as used herein refers to physically discrete units suited as unitary dosages for the subject to be treated; each unit containing a predetermined quantity of active compound calculated to produce a desired therapeutic effect in association with the pharmaceutical carrier or excipient.

The invention provides kits comprising the human CD40 antibodies, nucleic acids encoding human CD40 antibodies or pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., two or more human CD40 antibodies.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions.

Kits of the invention therefore can additionally include labels or instructions for using the kit components in a method of the invention. Instructions can include instructions for practicing any of the methods of the invention described herein including treatment, detection, monitoring or diagnostic methods. Thus, for example, a kit can include a human CD40 antibody that modulates one or more activities of CD40 in a pack, or dispenser together with instructions for administering the antibody in a treatment method of the invention. Materials for labeling the CD40 antibody are optionally included in the kit as are a control or standardization sample that contains a known amount of CD40 or a reaction cocktail that provides suitable conditions for performing the assay.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a growth medium (e.g., for a CD40 antibody producing hybridoma), buffering agent, or a preservative or a stabilizing agent in a pharmaceutical formulation containing a human CD40 antibody. Each component of the kit can be enclosed within an individual container and all of the various containers can be within a single package. Invention kits can be designed for cold storage. Invention kits can further be designed to contain human CD40 antibody producing hybridoma or other host cells. The cells in the kit can be maintained under appropriate storage conditions until the cells are ready to be used. For example, a kit including one or more hybridoma or other cells can contain appropriate cell storage medium (e.g., 10–20% DMSO in tissue culture growth medium such as DMEM, α-MEM, etc.) so that the cells can be thawed and grown.

Human CD40 antibodies of the invention are useful for detecting or purifying CD40 polypeptides. Such methods include contacting a sample suspected of containing CD40 (in solution, in solid phase, in vitro or in vivo, or in an intact cell or organism) with a CD40 antibody under conditions allowing binding and detecting the presence of CD40, or purifying the bound CD40 polypeptide.

The invention therefore also provides methods for detecting the presence of CD40 in a test sample. In one embodiment, a method includes contacting a sample having or suspected of having CD40 with a human CD40 antibody under conditions allowing detection of CD40 in the sample and determining whether CD40 is present in the test sample.

Detection of CD40 can be performed by conventional methods such as immunoprecipitation, western blotting, immunohistochemical staining or flow cytometry. For example, a labeled human CD40 antibody can be incubated with the sample and then purified using protein A or protein G under conditions allowing association between the antibody and CD40. The bound CD40 can be dissociated from the antibody and quantified by gel fractionation followed by staining (silver or coomasie blue staining). Alternatively, a sample may be fractionated via gel electrophoresis and blotted onto a membrane in order to transfer fractionated proteins. The anti-CD40 antibody is incubated with the membrane and a second antibody, modified to be detectable, is used to detect the anti-CD40 antibody bound to CD40 present on the membrane.

CD40 detection methods are useful in diagnostic protocols for detecting CD40. For example, where increased or decreased levels of CD40 are associated with development, the presence of or progression of a pathology, invention antibodies can be used to detect any increase or decrease in CD40. In addition, where it is desired to monitor levels of CD40 following a treatment therapy that increases or decreases CD40 levels, invention antibodies can be used to detect an increase or decrease in CD40 levels before, during or following the treatment, over long or short term.

The invention therefore also provides methods for detecting the presence of CD40 in a test sample of a subject (containing biological fluid, cells, or a tissue or organ sample such as a biopsy). In one embodiment, a method includes contacting a sample having or suspected of having CD40 obtained from a subject with a human CD40 antibody under conditions allowing detection of CD40 and determining whether CD40 is present in the test sample from the subject.

In addition, human CD40 antibodies of the invention are useful for detecting the presence of a disorder associated with increased or decreased CD40 expression in a human. The invention therefore provides methods for diagnosing a pathology that is characterized, in part, by increased or decreased CD40 expression. In one embodiment, a method includes contacting a sample having or suspected of having CD40, wherein the sample is obtained from or present in a human, with a human CD40 antibody, and detecting the presence of increased or decreased CD40 expression in the sample relative to a control, thereby detecting the presence of a disorder associated with increased or decreased CD40 expression in the human. A sample can be obtained from a matched subject that does not have the pathology in order to make a comparison in CD40 levels. A normal range of CD40 levels can be determined by sampling a statistically significant number of normal matched subjects. Well known methods using antibodies to detect the presence and amount of bound antigen are known in the art and can be used to detect the presence of CD40 (see, for example, Harlow and Lane, supra, 1988).

The identification of a CD40 associated pathology can allow for intervention therapy using an invention CD40 antibody alone, or in combination with other forms of therapy appropriate for treating the pathology.

Human CD40 antibodies may also be utilized to monitor the presence of circulating soluble CD40 which has been administered to a subject, or to measure in vivo levels of CD40 in subjects. For example, serum suspected of containing soluble CD40 is incubated with a CD40 antibody, as described above, under conditions allowing binding to occur, and the presence of soluble CD40 is determined. Presence of CD40 indicates the presence of the CD40 in the subject's serum. Serum can be obtained from a subject before the subject is administered CD40 in order to make a comparison.

Deposits were made with American Type Culture Collection (ATCC), 10801 University Blvd., Manassas, Va., 20110-2209, U.S.A. Deposit designations and dates of deposit are as follows: number 11 or 72 (produced by hybridomas ATCC PTA-2308 and PTA-23 09, respectively, deposited Jul. 28, 2000); F1-102 (produced by hybridoma ATCC PTA-3337, deposited Apr. 24, 2001); F4-465 (produced by bybridoma ATCC PTA-33 38, deposited Apr. 24, 2001); F2-103 (ATCC PTA-3302 and PTA-3303, heavy and light chain, respectively, deposited Apr. 19, 2001); F5-77 (ATCC PTA-3304 and PTA-3305, heavy and light chain, respectively, deposited Apr. 19, 2001); and F5-157 (ATCC PTA-3306 and PTA-3307, heavy and light chain, respectively, deposited Apr. 19, 2001).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a CD40 antibody" includes a plurality of such antibodies and reference to "a CD40 activity" can include reference to one or more CD40 activities or functions, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes cells and CD40 expression constructs used to produce human antibodies that bind to human CD40, and CD95 expression and DNA synthesis assays.
Cells and Antibodies EL-4 cells were a gift from Dr. Stephen Schoenberger. Ramos B cells and G28.5 hybridoma were purchased from ATCC. Human peripheral B cells were purchased from AllCells, LLC (Berkeley, Calif.). P-RE conjugated—and HRP conjugated—goat anti-human γ specific antibody, and HRP conjugated—goat anti-human κ specific antibody were purchased from Southern Biotechnology Associates, Inc. (Birmingham, Ala.). FITC conjugated-anti-human CD40 antibody and P-RE conjugated-anti-human CD95 antibody were purchased from Pharmingen (San Diego, Calif.)
Expression of Human CD40: Fc Fusion Protein Human CD40 cDNA was used as a template, and PCR was performed to amplify a fragment covering the extracellular domain of human CD40 with primers (5'-CCCAGATCTGTCCATCCAGAACCACCCACTGCATG CAGAG-3'; SEQ ID NO:1 and 5'-ACAAGATCTGGGCTC TACGTATCTCAGCCGATCCTGGGGAC-3'; SEQ ID NO:2) at 95° C. for 5 sec, 550° C. for 30 sec and 72° C. for 30 sec for 20 cycles. The amplified cDNA was inserted into pFastBac™ donor plasmids (Gibco BRL) at the 3'-end of a honeybee melityin signal peptide and at the 5' end of the Fc sequence of either human IgGl or mouse IgG2b. Recombinant baculoviruses carrying the human CD40-Fc gene fusion were generated according to the manufacturer's instructions. Tn5 insect cells were infected with the viruses and cultured for 4 days. Insect cell supernatant was mixed with Protein G Sepharose (Amersham Pharmacia). After overnight incubation at 4° C. with gentle shaking, the sepharose was packed into a column and washed with 20 vol of PBS. The human CD40-Fc fusion protein was eluted with 20 mM Glycine-HCl (pH 3.0).

For cell surface expression of human CD40, pEF-Bos vector carrying the full length cDNA of the human CD40 gene was obtained from Randolph J. Noelle. The full length cDNA was cut at the XbaI site and inserted into a pCDNA3 a vector and transfected into EL4 cells. Stable transfectants were selected with 0.5 mg/ml G418 (Gibco BRL). Expression of CD40 was confirmed by FACS analysis using FITC-conjugated anti-human CD-40 antibody (Pharmingen).
CD95 Expression on Ramos B Cells 2.5×10$^6$ Ramos B cells were plated onto a 48 well plate. Purified IgG or soluble human CD40L (ALEXIS San Diego, Calif.) was added. After incubating for 24 hours, cells were collected and stained with P-RE conjugated anti-human CD95 antibody, and analyzed by FACS scan.

DNA Synthesis

DNA synthesis was measured by $^3$H-thymidine incorporation. Human peripheral blood B cells ($5 \times 10^4$ cells/well) were plated onto 96 well plates with 10 UCi/ml [$^3$H] thymidine, 10 ng/ml human IL-4, anti-CD40 antibody and/or soluble CD40L. After 3 days in culture, cells were harvested using a Tomtec cell harvester (EG&G), and the counts were measured by a Betaplate liquid scintillation counter (Pharmacia).

Example 2

This example describes the production of human monoclonal antibodies to human CD40 using human transchromosomic mice.

Human transchromosomic mice (Tomizuka et al., Proc. Natl. Acad. Sci. USA 97:722 (2000) and Tomizuka et al., Nat. Genet. 16:133 (1997)) harboring human chromosome fragments containing the immunoglobulin region were immunized subcutaneously with 100 ug of hCD40-hFc in CFA. Mice were boosted subcutaneously with 100 ug of hCD40-hFc in IFA after 10 and 20 days. A final intravenous injection of 100 ug of hCD40-hFc without adjuvant was given on day 37.

Antibody titers were determined by ELISA. In brief, human CD40-mouse Fc fusion protein was coated on a plate at a concentration of 1.4 ug/ml with carbonate buffer at 37° C. for 1 h. After washing 3 times with PBS/0.1% Tween 20, plates were blocked with PBS/1% BSA at 37° C. Diluted antibody or serum was added to the wells and the plates were incubated at 37° C. for 1 h. After washing 3 times, diluted HRP conjugated goat anti-human gamma chain specific antibody, or HRP conjugated goat anti-human kappa chain specific antibody, was added to the wells and incubated for 1 h. at 37° C. After washing 3 times, TMB substrate solution (DAKO) was added to the wells and incubated for 30 min. at room temperature. The optical density at 450 nm was measured by a microplate reader. Titer increases were detected in all 6 mice after the $3^{rd}$ boosting.

Two of the 6 mice showing the highest antibody titers were selected for production of monoclonal antibodies. Spleens were harvested and fused to a myeloma cell line (SP2/O—Ag14) and fusions plated onto 96 well plates (18 plates in total). Approximately 1500 hybridoma wells were screened by FACS analysis and ELISA, using diluted HRP conjugated goat anti-human γ specific antibody, or HRP conjugated goat anti-human κ specific antibody as the secondary antibody. Cells positive for either the heavy chain or the κ chain were transferred to 24 well plates, and expanded.

For antibody purification, hybridomas were cultured in CELLine (IBS) and antibody was purified using a protein G affinity resin. Supernatants from hybridomas which were positive by ELISA, were also analyzed by cell staining assay, using EL-4 cells which express human CD40 on their surface. The expression of CD40 was confirmed with FITC conjugated anti-human CD40 antibody. Hybridoma supernatants were added to $5 \times 10^5$ EL4 cells, and incubated at 4° C. for 3 min. Cells were washed three times with PBS/5% FBS and 0.1 ug of R-PE conjugated anti human gamma antibody was added and incubated at 4° C. for 30 min. After washing three times, cells were analyzed for staining by FACS scan. The analysis revealed that 45 hybridomas were positive.

The positive hybridoma clones were subjected to limiting dilutions a minimum of three times, and 13 single clones were isolated. From the 13 single clones, four antibodies (Nos. 11, 20, 72, and 366) were isolated. Cell staining assays indicated that all four of the antibodies stained cells expressing cell surface human CD40 (FIG. 1). Although human Fc should be non-immunogenic in Tc mice, a negative screen for Fc reactivity was conducted by ELISA using a human CD40-mouse Fc fusion protein.

Example 3

This example describes the modulation of CD40 activity with the CD40 antibodies. This example also describes the CD40 binding affinity of the CD40 antibodies.

Figure 2A:
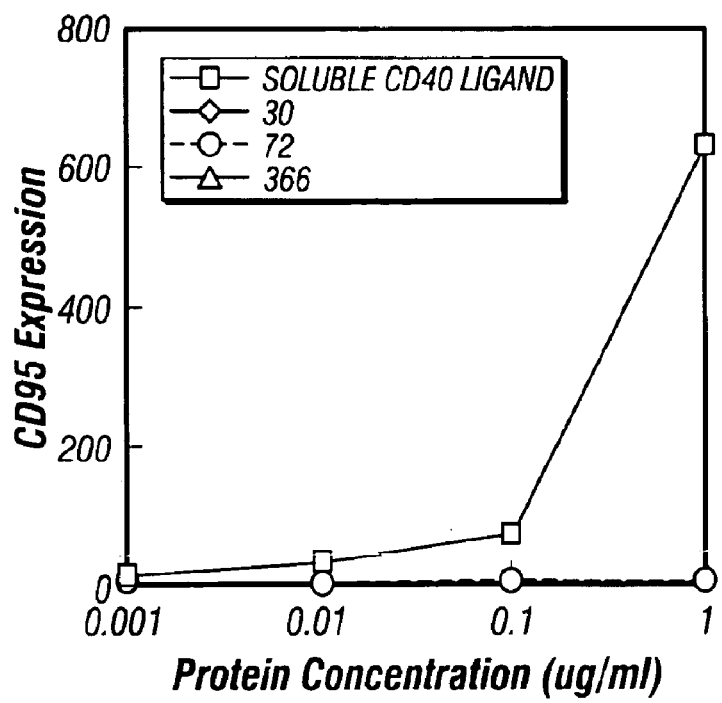
FIG. 2 shows the effect of human anti-human CD40 antibody nos. (A) 30, 72, 366, and (B) no. 11, 5C3 and G28 on Ramos B cell CD95 expression in comparison to CD40L. Antibody or soluble CD40 ligand was added at the concentrations indicated on the horizontal axis. Expression of CD95 was measured by FACS as described in Example 1. The vertical axis represents the peak value of CD95 expression.
Figure 2B:
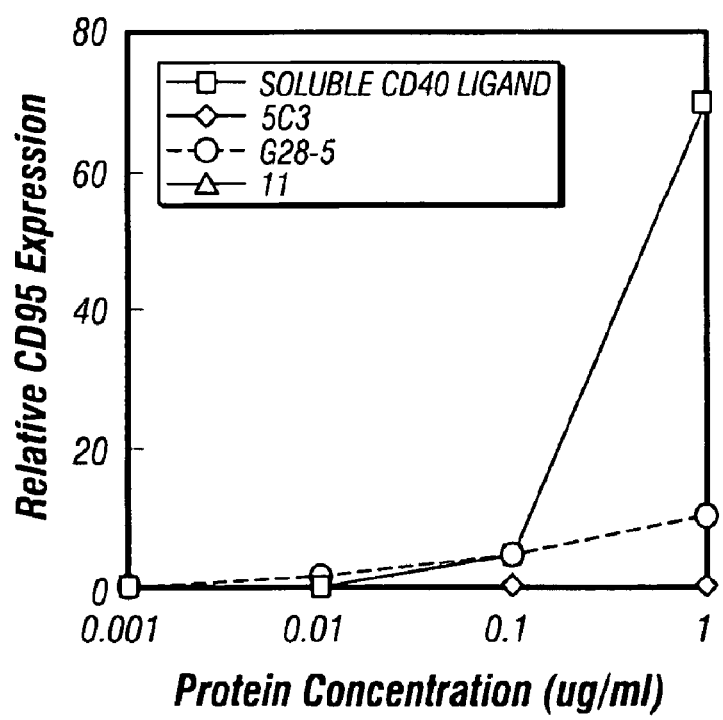

Ramos B cells, a human B lymphoma cell line that expresses CD95 upon stimulation with either soluble CD40L or agonistic anti-CD40 antibody (Schattner et al., J. Exp. Med. 1182:1557 (1995)) were used to analyze activity of the four antibodies (Nos. 11, 30, 72, and 366). In brief, Ramos B cells were incubated with the purified antibodies and CD95 expression was measured after culturing for 24 h (FIGS. 2A and 2B). The results indicate that expression of CD95 was induced by control soluble CD40 ligand and G28-5, an agonistic mouse anti-human CD40 antibody. In contrast, human antibody nos. 11, 30, 72, and 366 were unable to induce detectable expression of CD95.

Figure 3:
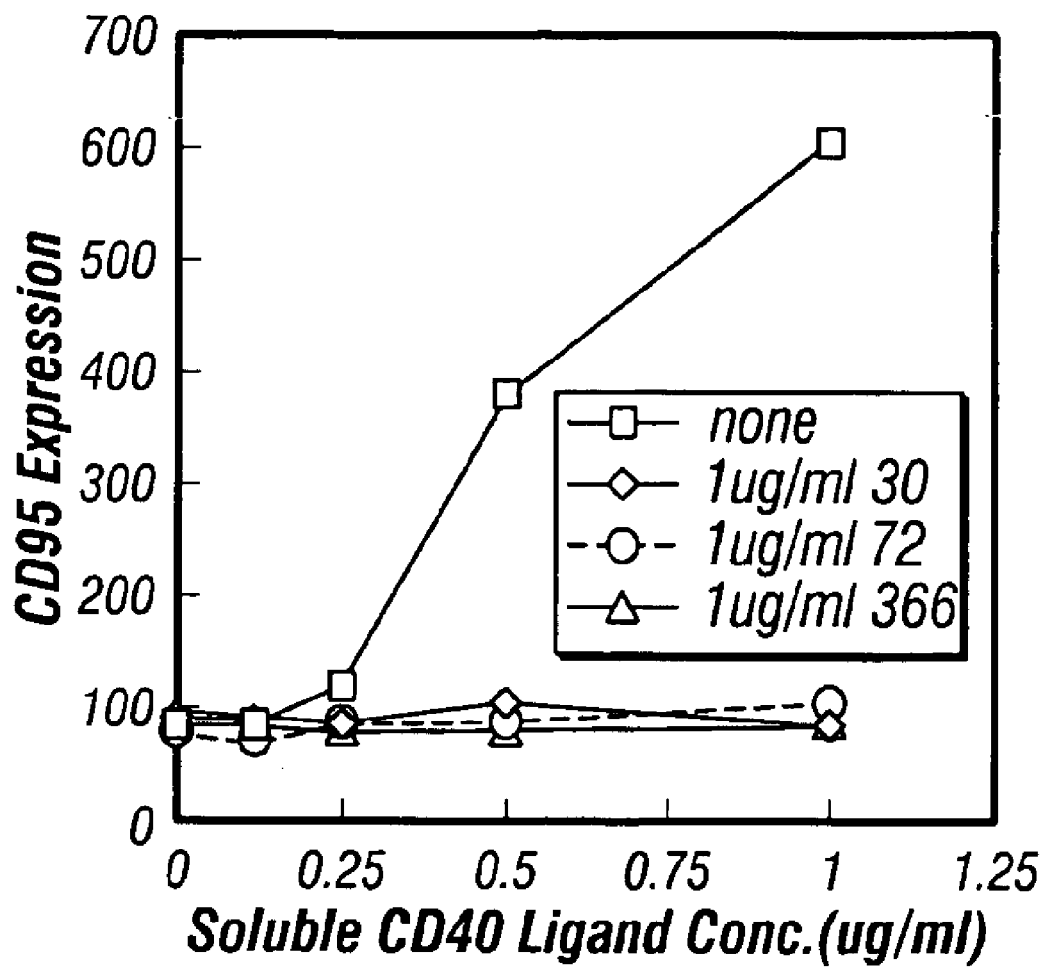
FIG. 3 shows the ability of human anti-human CD40 antibody nos. 30, 72 and 366 to block CD95 expression in Ramos B cells. Antibodies were added at the indicated concentration along with soluble CD40 ligand. Expression of CD95 was measured by FACS as described in Example 1. The horizontal axis indicates the concentration of soluble CD40 ligand and the vertical axis indicates the peak value of CD95 expression.

To determine the ability of the CD40 antibodies to block binding of CD40L to CD40, Ramos B cells were incubated with 1 ug/ml purified antibody and soluble CD40L. After culturing for 24 h, expression of CD95 was measured. Three antibodies (Nos. 30, 72, and 366) completely inhibited induction of CD95 expression by soluble CD40L (FIG. 3).

Figure 4A:
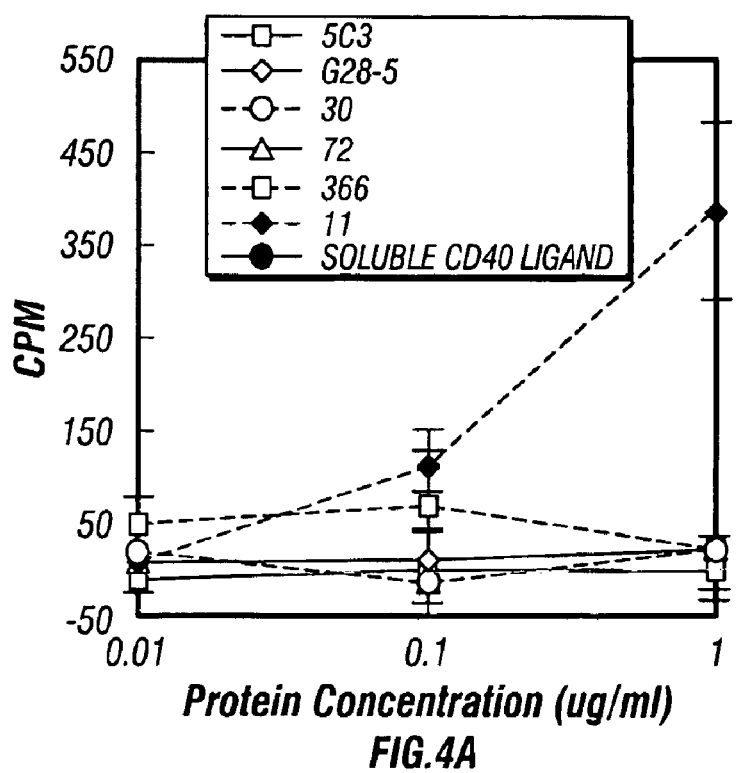
FIG. 4 shows the effect of human anti-human CD40 antibody on human peripheral B cell proliferation in the (A) presence or (B) absence of CD40L (1 ug/ml) for 3 days. The horizontal axis indicates protein antibody or soluble CD40L concentration. The vertical axis indicates [$^3$H]-thymidine incorporation by human B cells, as described in Example 1.
Figure 4B:
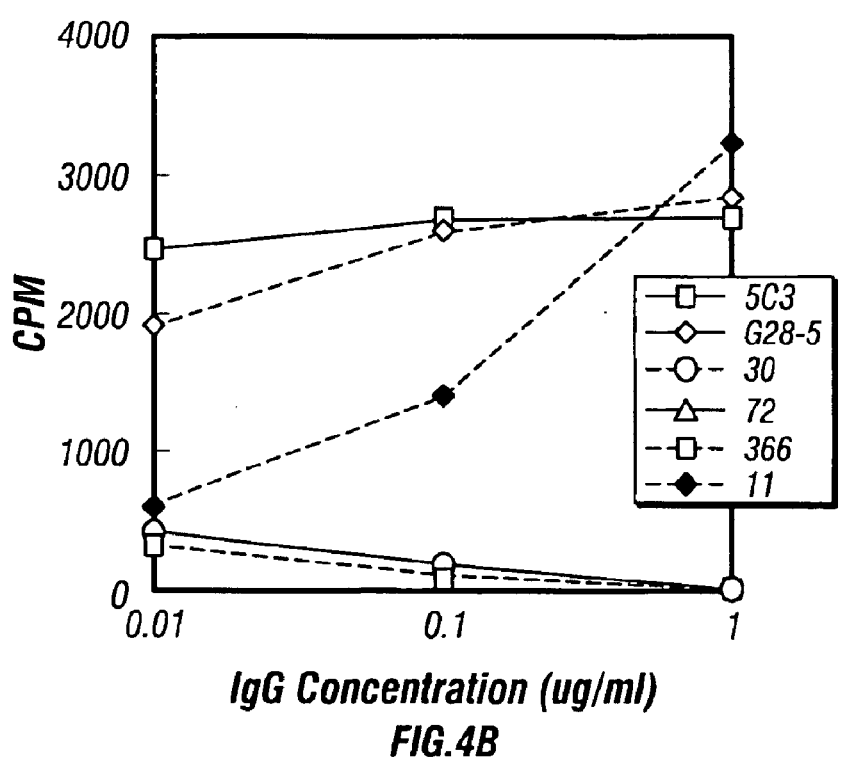

The effect of anti-human CD40 antibodies on the proliferation of human peripheral B cells was determined as described above. None of the four antibodies induced human B-cell proliferation without soluble CD40L. However, in cultures containing 1 ug/ml soluble CD40L, antibody No. 11 strongly enhanced human B-cell proliferation in a manner similar to the murine antibody G8-5 or 5 C3, an antibody previously reported to enhance B-cell proliferation (FIG. 4A). The other three human antibodies (Nos. 30, 72, and 366) completely inhibited the effect of soluble CD40L (FIG. 4B).

The production of a human anti-human CD40 antibody which enhances the proliferation of human peripheral B cells in combination with CD40L also has therapeutic implications. In this regard, other groups have reported on the agonistic activity of mouse anti-human CD40 antibodies such as 5C3 or G28-5 (Pound et al., Int. Immunol. 11:11 (1999)). Human antibody No. 11 did not inhibit the binding of soluble CD40L to CD40, but it did strongly enhance B-cell proliferation in combination with CD40L. Based on these characteristics, human antibody no. 11 is in the same class of antibodies as 5C3—an agonistic antibody that does not block the binding of the native ligand. Such an antibody is suitable for anti-tumor or anti-virus therapy.

The affinity of anti-CD40 antibody No. 30 was determined by BiaCore™ analysis. Human CD40-mouse FC fusion protein was crosslinked to a sensor chip and the affinity was measured according to the manufacturer's protocol. The Kd value was 0.8–4 nM.

The anti-CD40 antibody hybridomas F1-102, F5-152 and F4-465 were tested by Ramos cell assay as described above. F1-102 and F5-152 were obtained from human CD40-Fc immunized Tc mouse and, therefore, expressed human kappa light chain. F4-465 was obtained from the HAC mouse (Kuroiwa et al., Nature Biotech., 10:1086 (2000)) and therefore expressed the human lambda light chain.

Figure 5A:
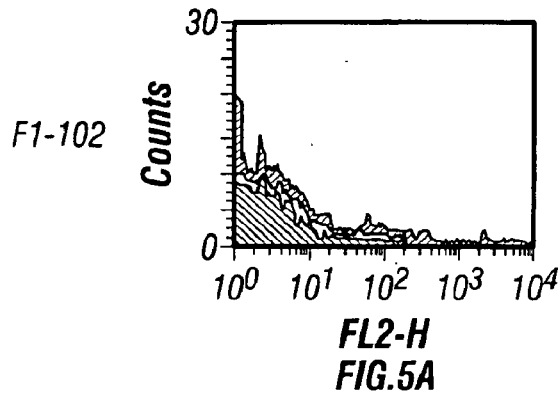
FIG. 5 shows Ramos cell CD95 staining activity following overnight incubation with (A) human IgG (filled histogram) or with F1-102 (lined histogram) antibody; and (B) CD40L and human IgG (filled histogram) or with F1-102 (lined histogram) antibody. F1-102 was purified from ascites fluid.
Figure 5B:
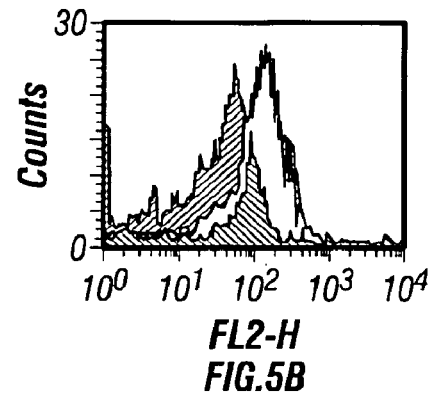
Figure 6A:
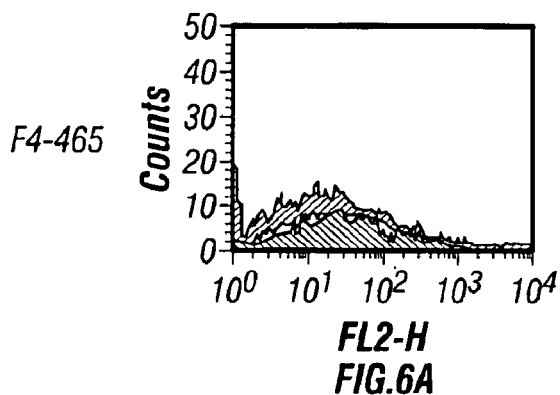
FIG. 6 shows Ramos cell CD95 staining activity following overnight incubation with (A) human IgG (filled histogram) or with F4-465 or F5-152 (lined histogram) antibody; and (B) CD40L and human IgG (filled histogram) or with F4-465 or F5-152 (lined histogram) antibody. F4-465 and F5-152 were purified from ascites fluid.
Figure 6B:
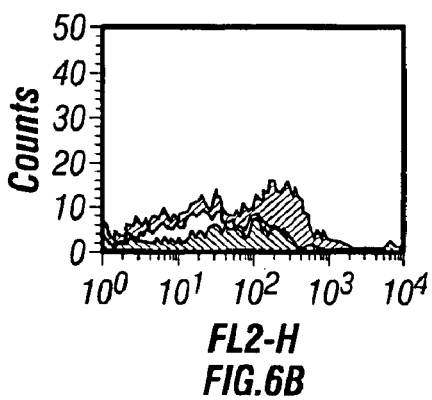
Figure 6C:
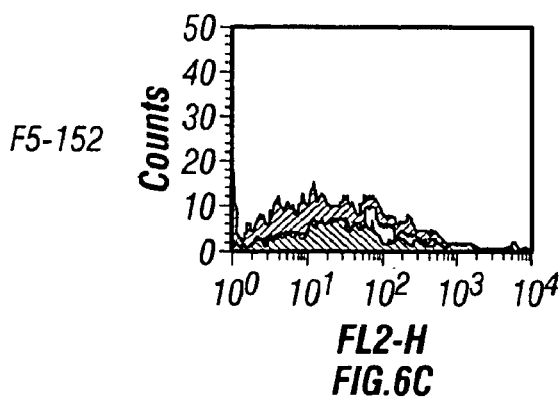
Figure 6D:
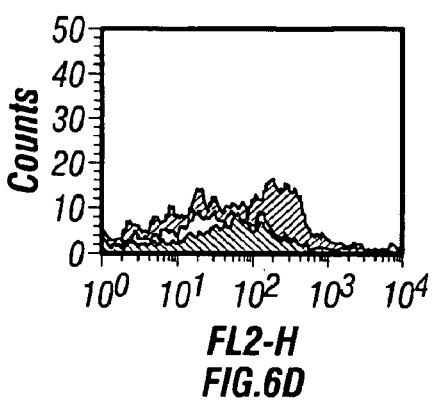
Figure 7A:
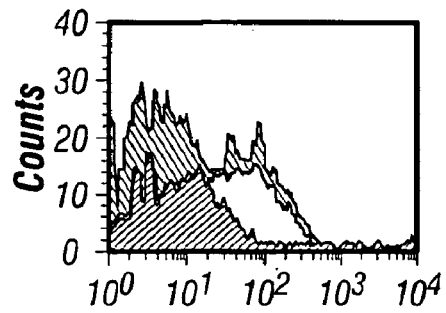
FIG. 7 shows Ramos cell CD95 staining activity following overnight incubation with (A) human IgG (filled histogram) or with F2-103, F5-157 or F5-77 (lined histogram) antibody; and (B) CD40L and human IgG (filled histogram) or with F2-103, F5-157 or F5-77 (lined histogram) antibody. F2-103, F5-157 and F5-77 were expressed in transiently transfected Cos cells.
Figure 7B:
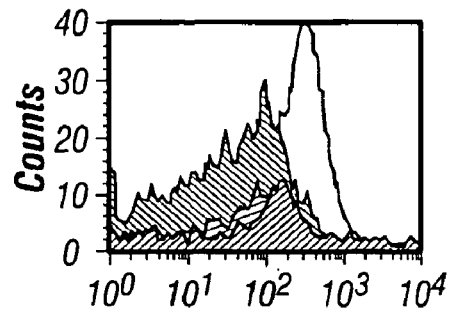
Figure 7C:
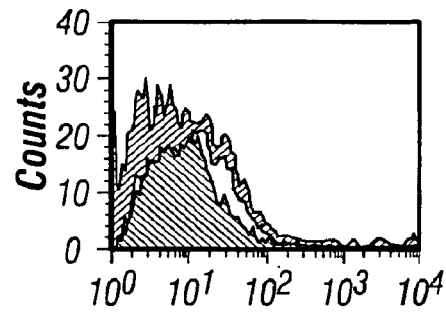
Figure 7D:
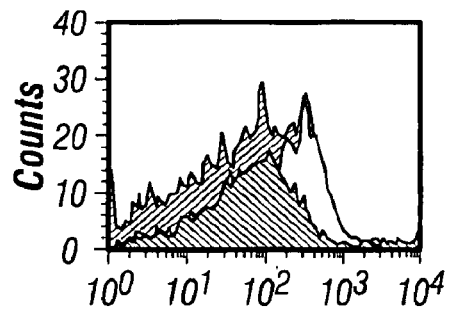
Figure 7E:
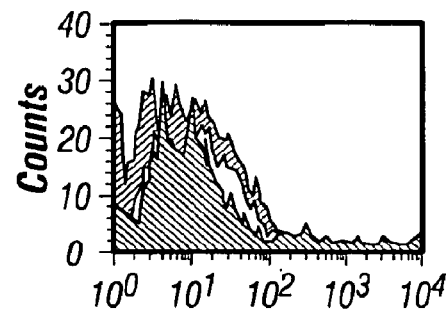
Figure 7F:
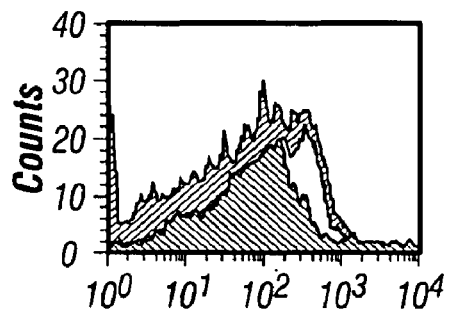

The results shown in FIGS. 5 and 6 indicate that the antibody produced by F1-102 and F5-152 stimulated CD95 expression on Ramos cells and enhanced the stimulatory effect of CD40L indicating that these antibodies are agonistic. In contrast, F4-465 failed to upregulate CD95 expression and blocked the stimulatory effect of CD40L. F4-465 is the first antagonistic antibody consisting of lambda chain.

Example 4

This example describes producing recombinant anti-CD40 antibodies in mammalian cell lines. This example also describes CD40 modulating activities of the recombinantly produced CD40 antibodies.

Recombinant antibodies were produced by cloning immunoglobulin (Ig) genes from hybridomas that produce anti-human CD40 antibodies and expressed in mammalian cells. In brief, total RNA was purified from each of hybridomas F2-103, F5-77 and F5-157 using Tri-Reagent™ according to the manufacturer's instructions (Molecular Research Center, Inc., Cincinnati, Ohio). Full length cDNA was synthesized from total KNA using the SMART RACE™ cDNA Amplification Kit (Clontech Laboratories, Inc., Palo Alto, Calif.) and Superscript II™ RT (GibcoBRL). The 5' variable regions of the human heavy and human light chains were isolated by PCR using 5'-RACE PCR as described by the manufacturer (Clontech Laboratories, Inc.). A universal primer mix supplied by the manufacturer was used for 5'-priming along with one of the following gene specific primers for 3'-priming. For amplification of all other heavy chains the gene specific primer was 5'-GTGCACGCCGCTGGTCAGGGCGCCTG-3' (SEQ ID NO:3). For amplification of kappa chains, the gene specific primer sequence was 5'-GTTGAAGCTCTTTGTGACGGGCGAGC-3' (SEQ ID NO:4). Full length PCR products were gel purified and blunt end ligated into SrfI cut PCR-Script™ (Stratagene, La Jolla, Calif.) or PCR-Blunt (Invitrogen, Carlsbad, Calif.) and sequenced by CFAR, Molecular Biology Core Facility (University of California, San Diego).

Human heavy and light chain variable sequences were subsequently cloned into N5KG1-Val LARK (IDEC) by PCR. The heavy chain sequences were cloned into the SalI and NheI sites using the 5' primer 5'-ACCGTGTCGACGGTGATCAGGACTGAACAG-3' (SEQ ID NO:5) for F5-77 (K1H1) and F5-157 (K3H3) or 5'-ACCGTGTCGACGCTGATCAGGACTGCACA-3' (SEQ ID NO:6) for F2-103 (K1H1) and the 3' primer 5'-AGTGCTAGCTGAGGAGACGGTGAC-3' (SEQ ID NO:7). The kappa chain variable sequences were cloned into the BglII and BsiWI sites using the 5' primer 5'-AACTCCAGATCTAGGGCAAGCAGTGGTAAC-3' (SEQ ID NO:8) and the 3' primer 5'-TATCCCGTACGGTTGATCTCCACCTTGGTC-3' (SEQ ID NO:9). The sequences of the antibody heavy and light chains produced by the indicated hybridomas are as follows:

```
F2-103-heavy

GCTGATCAGGACTGCACACAGAGAACTCACCATGGAGTTTGGGCTGAGCTGGGTTTTCCTTGTTGCTATTTT (SEQ ID NO: 10)

AAAAGGTGTCCAGTGTGAGGTGCAGCTGGTGGAGTCCGGGGGAGGCTTAGTTCAGCCTGGGGGGTCCCTGAG

ACTCTCCTGTGCAGTCTCTGGATTCACCTTCAGTACCTACTGGATGCACTGGGTCCGCCAAGCTCCAGGGAA

GGGGCTGGTGTGGGTCTCACGTATTAATAGTGATGGGAGTAGCACAACCTACGCGGACTCCGTGAAGGGCCG

ATTCACCATCTCCAGAGACAACGCCAAGAACACGCTGTATCTGCAAATGAACAGTCTGAGAGCCGAGGACAC

GGCTGTGTATTACTGTGCAAGAGATAGAGTACTATGGATCGGGGAGTTATCCTACTACGGTATGGACGTCTG

GGGCCAAGGGACCACGGTCACCGTCTCCTCAGCTAGCACCAAGGGCCCATCGGTCTTCCCCCTGGCACCCTC

CTCCAAGAGCACCTCT

F2-103-light

GGGGAGTCAGACCCAGTCAGGACACAGCATGGACATGAGGGTCCCCGCTCAGCTCCTGGGGCTCCTGCTGCT (SEQ ID NO: 11)

CTGGCTCCCAGGTGCCAAATGTGACATCCAGATGACCCAGTCTCCTTCCACCCTGTCTGCATCTGTAGGAGA

CAGAGTCACCATCACTTGCCGGGCCAGTCAGAGTATTAGTAACTGGTTGGCCTGGTATCAGCAGAAACCAGG

GAAAGCCCCTAADCTCCTGCTCTATAAGGCATCTGGTTTAGAAAGTGGGGTCCCATCAAGGTTCAGCGGCAG

TGGATCTGGGACAGAATTCACTCTCACCATCAACAGCCTGCAGCCTGATGATTTTGCAACTTATTACTGCCA

ACAGTCTAATAGTTATTCGTGGACGTTCGGCCACGGGACCAAGGTGGAAATCAAACGTACGGTGGCTGCACC

ATCTGTCTTCATCTTCCCGCCATCTGATGAGCAGTTGAAATCTGGAACTGCCTCTGTTGTGTGCCTGCTGAA

TAACTTCTATCCCAGAGAGGCCAAAGTACAGTGGAAGGTGGATAACGCCCTCCAATCGGGTAACTCCCAGGA

GAGTGTCACAGAGCAGGACAGCAAGGACAGCACCTACAGCCTCAGCAGCACCCTGACGCTGAGCAAAGCAGA

CTACGAGAAACACAAAGTCTACGCCTGCGAAGTCACCCATCAGGGCCTGA
```

-continued

F5-157-heavy

GGTGATCAGGACTGAACAGGGAGAACTCACCATGGAGTTTGGGCTGGGCTGGCTTTTTCTTGTGGCTATTTT (SEQ ID NO: 12)
AAAAGGTGTCCAGTGTGAGGTGCAGCTGTTGGAGTCTGGGGGAGGCTTGGTACAGCCTGGGGGGTCCCTGAG
ACTCTCCTGTGCAGCCTCTGGATTCGCCTTTAGCAGCTATGCCATGAGCTGGGTCCGCCAGGCTCCAGGGAA
GGGGCTGGAGTGGGTCTCAGCTATTAGTGGTAGTGGTGGTAGCACATACTACGCAGACTCCGTGAAGGGCCG
GTTCACCATCTCCAGAGACAATTCCAAGAACACGCTGTATCTGCAAATGAACAGCCTGAGAGCCGAGGACAC
GGCCGTATATTACTGTGCGAAAGATGGGGGGTACTATGGTTCGGGGAGTTATGGGTACTTTGACTACTGGGG
CCAGGGAACCCTGGTCACCGTCTCCTCAGCTAGCACCAAGGGCCCATCGGTCTTCCCCCTGGCACCCTCCTC
CAAGAGCACCTCTGGGGGCACAGCGGCCCTGGGCTGCCTGGTCAAGGACTACTTCCCCGAACCGGTGACGGT
GTCG

F5-157-light

CAACGCAGAGTACGCGGGGAGGAGTCAGACCCAGTCAGGACACAGCATGGACATGAGGGTCCCCGCTCAGCT (SEQ ID NO: 13)
CCTGGGGCTCCTGCTGCTCTGGTTCCCAGGTTCCAGATGCGACATCCAGATGACCCAGTCTCCATCTTCCGT
GTCTGCATCTGCAGGAGACAGAGTCACCATCACTTGTCGGGCGAGTCAGGGTATTAGCAGCTGGTTAGCCTG
GTATCAACAGAAACCAGGGAAAGCCCCTAAGCTCCTGATCTATGCTGGATCCAGTTTGCAAAGTGGGGTCCC
ATCAAGGTTCAGCGGCAGTGGATTTGGGACAGATTTCACTCTCACCATCGGCAGCCTGCAGCCTGAAGATTT
TGCAACTTACTATTGTCAACAGGCTAGCAGTTTCCCTCGGACGTTCGGCCAAGGGACCAAGGTGGAGATCAA
ACGTACGGTGGCTGCACCATCTGTCTTCATCTTCCCGCCATCTGATGAGCAGTTGAAATCTGGAACTGCCTC
TGTTGTGTGCCTGCTGAATAACTTCTATCCCAGAGAGGCCAAAGTACAGTGGAAGGTGGATAACGCCCTCCA
ATCGGGTAACTCCCAGGAGAGTGTCACAGAGCAGGACAGCAAGGACAGCACCTACAGCCTCAGCAGCACCCT
GACGCTGAGCAAAGCAGACTACGAGAAACACAAAGTCTACGCCTGCGAAGTCACCCATCAGGGCCTGA

F5-77-heavy

GGTCTATATAAGCAGAGCTGGGTACGTCCTCACATTCAGTGATCAGCACTGAACACAGACCCGTCGACGGTG (SEQ ID NO: 14)
ATCAGGACTGAACAGAGAGAACTCACCATGGAGTTTGGGCTGAGCTGGCTTTTTCTTGTGGCTATTTTAAAA
GGTGTCCAGTGTGAGGTGCAGCTGTTGGAGTCTGGGGGAGGCTTGGTACAGCCTGGGGGGTCCCTGAGACTC
TCCTGTGCAGCCTCTGGATTCACCTTTAGCAGCTATGCCATGAGCTGGGTCCGCCAGGCTCCAGGGAAGGGG
CTGGAGTGGGTCTCAGCTATTAGTGGTAGTGGTGGTAGCACATACTACGCAGACTCCGTGAAGGGCCGGTTC
ACCATCTCCAGAGACAATTCCAAGAACACGCTGTATCTGCAAATGPACAGCCTGAGAGCCGAGGACACGGCC
GTATATTACTGTGCGAAAGATGGGGGGTACTATGGTTCGGGGAGTTATGGGTACTTTGACTACTGGGGCCAG
GGAACCCTGGTCACCGTCTCCTCAGCTAGCACCAAGGGCCCATCGGTCTTCCCCCTGGCACCCTCCTCCAAG
AGCACCTCTGGGGGCACAGCGGCCCTGGGCTGCCTGGTCAAGGACTACTTCCCC

F5-77-light

CAAGCAGTGGTAACAACGCAGAGTACGCGGGGGGAGTCAGACCCAGTCAGGACACAGCATGGACATGAGGGT (SEQ ID NO: 15)
CCCCGCTCAGCTCCTGGGGCTCCTGCTGCTCTGGTTCCCAGGTTCCAGATGCGACATCCAGATGACCCAGTC
TCCATCTTCCGTGTCTGGATCTGTAGGAGACAGAGTCACCATCACTTGTCGGGCGAGTCAGGGTATTAGCAG
CTGGTTAGCCTGGTATCAGCAGAAACCAGGGAAAGCCCCTAAGCTCCTGATCTATGCTGGATCCAGTTTGCA
AAGTGGGGTCCCATCAAGGTTCAGCGGCAGTGGATTTGGGACAGATTTCACTCTCACCATCAGCAGCCTGCA
GCCTGAAGATTTTGCAACTTACTATTGTCAACAGGCTAGCAGTTTCCCTCGGACATTCGGCCAAGGGACCAA
GGTGGAGATCAAACGTACGGTGGCTGCACCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTACAGTGGAAGGTGGA

-continued

TAACGCCCTCCAATCGGGTAACTCCCAGGAGAGTGTCACAGAGCAGGACAGCAAGGACAGCACCTACAGCCT

CAGCAGCACCCTGACGCTGAGCAAAGCAGACTACGAGAAACACAAAGTCTACGCCTGCGAAGTCACCCATCA

GGGCCTGA

Expression plasmids were transiently transfected into Cos-1 cells by electroporation. Briefly, $3 \times 10^6$ cells were resuspended in 0.7 ml of serum-free DMEM containing 30 ug of plasmid DNA and placed into a 0.4 cm BioRad™ cuvette #165-2088. Cells were electroporated in a Gene Pulser II™ (BioRad™) set at 240 volts, capacitance=0.950 with a constant time of 15–25 msec. After pulsing, the cells were transferred to 10 cm dishes containing 10 ml DMEM, 10% FBS. Conditioned media containing human Ig was harvested 72 hours later.

Human antibodies were purified from culture media using Protein A sepharose™ 4 Fast Flow (Amersham #17-0618-02). Briefly, conditioned media was loaded onto a 0.5 ml column. The flow through fraction was re-loaded onto the column two additional times. The column was washed with 10 ml PBS and antibody was eluted with 2.5 ml of 20 mM Glycine, pH 3.0. Elution fractions were collected in a volume of 0.5 ml and neutralized immediately with 25 ul of 1M Tris, pH 9.0. Protein containing fractions were pooled and buffer exchanged into 1 ml PBS using a NAP-5 column according to the manufactures instructions (NAP-5, Pharmacia Biotech). Antibody concentrations were determined by absorbance at 280 nm or by a standard Bradford assay. The ability of each purified antibody to bind human CD40 was confirmed by FACS using EL-4 cells as described previously in this document. Pyrogen levels of the samples were determined to be less than 0.03 EU per 10 ug according to a Limulus Amebocyte Lysate (LAL) assay (Associates of Cape Cod, Inc., Falmouth, Mass.).

The results in FIG. 7 indicate that each of the human antibodies produced by hybridomas F2-103, F5-77 and F5-157 stimulate CD95 expression by Ramos cells. Like CD40 antibody no. 11 and F1-102 and F5-152, antibodies F2-103, F5-77 and F5-157 are therefore also useful in stimulating CD40 activity.

The results show that transchromosomic mice can be used to produce of high affinity functional human CD40 antibodies that modulate one or more activities of CD40. The antibodies that inhibit CD40L induced expression of CD95 on Ramos cells or proliferation of human peripheral B cells are likely to be effective therapeutic agents in the treatment of CD40-associated disorders treatable by decreasing a CD40 activity. The antibodies that stimulate CD40L induced expression of CD95 on Ramos cells or proliferation of human peripheral B cells are likely to be effective therapeutic agents in the treatment of CD40-associated disorders treatable by increasing CD40 activity.

What is claimed is:

1. A human monoclonal antibody or a CD40-binding fragment thereof, wherein the antibody is denoted number 11, which is produced by hybridoma ATCC PTA-2308.

2. A human monoclonal antibody, wherein the antibody comprises the heavy-chain variable sequence and the light-chain variable sequence of the antibody denoted as number 11, which is produced by hybridoma ATCC PTA-2308.

3. A human monoclonal antibody, wherein the antibody comprises the heavy-chain valuable sequence and the light-chain variable sequence encoded by the pair of sequences set forth as SEQ ID NO: 10 and SEQ ID NO: 11; SEQ ID NO: 12 and SEQ ID NO: 13; or SEQ ID NO: 14 and SEQ ID NO: 15.

4. A human monoclonal antibody, wherein the antibody comprises a heavy-chain variable sequence and a light-chain valuable sequence encoded by heavy and light chain sequences selected from F2-103-heavy chain (ATCC PTA-3302) and F2-103-light chain (ATCC PTA-3303); F5-77-heavy chain (ATCC PTA-3304) and F5-77-light chain (ATCC PTA-3305); and F5-157-heavy chain (ATCC PTA-3306) and F5-157-light chain (ATCC PTA-3307).

5. A hybridoma denoted as ATCC PTA-2308.

6. A hybridoma denoted as ATCC PTA-2309.

7. A hybridoma denoted as ATCC PTA-3337.

8. A hybridoma denoted as ATCC PTA-3338.

9. A cell line denoted as ATCC PTA-3302.

10. A cell line denoted as ATCC PTA-3303.

11. A cell line denoted as ATCC PTA-3304.

12. A cell line denoted as ATCC PTA-3305.

13. A cell line denoted as ATCC PTA-3306.

14. A cell line denoted as ATCC PTA-3307.

15. A human monoclonal antibody or a CD40-binding fragment thereof, wherein the antibody is denoted number 72, which is produced by hybridoma ATCC PTA-2309.

16. A human monoclonal antibody or a CD40-binding fragment thereof, wherein the antibody produced by a hybridoma denoted as F1-102 (ATCC PTA-3337).

17. A human monoclonal antibody or a CD40-binding fragment thereof, wherein the antibody produced by a hybridoma denoted as F4-465 (ATCC PTA-3338).

18. A human monoclonal antibody or a CD40-binding fragment thereof, wherein the antibody is denoted as F2-103, in which heavy chain of the antibody is produced by ATCC PTA-3302, and in which light chain of the antibody is produced by ATCC PTA-3303.

19. A human monoclonal antibody or a CD40-binding fragment thereof, wherein the antibody is denoted as F5-17, in which the heavy chain of the antibody is produced by ATCC PTA-3304, and in which the light chain of the antibody is produced by ATCC PTA-3305.

20. A human monoclonal antibody or a CD40-binding fragment thereof, wherein the antibody is denoted as F5-157, in which the heavy chain of the antibody is produced by ATCC PTA-3306, and, in which the light chain of the antibody is produced by ATCC PTA-3307.

21. A detectably labeled human monoclonal antibody or a CD40 binding fragment thereof, wherein the antibody or fragment is the antibody or fragment of any of claims 18–20.

22. A human monoclonal antibody, wherein the antibody comprises the heavy-chain variable sequence and the light-chain variable sequence of the antibody denoted as number 72, which is produced by hybridoma ATCC PTA-2309.

23. A human monoclonal antibody, wherein the antibody comprises the heavy-chain variable sequence and the light-chain variable sequence of the antibody produced by a hybridoma denoted as F1-102(ATCC PTA-3337).

24. A human monoclonal antibody, wherein the antibody comprises the heavy-chain variable sequence and the light-chain variable sequence of the antibody produced by a hybridoma denoted as F4-465 (ATCC PTA-3338).

25. The human monoclonal antibody fragment of any of claims 1 or 15–20, wherein the fragment comprises an scFv, Fab, Fab', or F(ab')$_2$ fragment.

26. A detectably labeled human monoclonal antibody, wherein the antibody is the antibody of any of claims 1 or 15–17.

27. A pharmaceutical formulation including the antibody of any of claims 1 or 15–20.

28. A host cell that expresses the antibody of any of claims 1 or 15–20.

29. A nucleic acid that encodes the antibody of any of claims 1 or 15–20.

30. A host cell containing the nucleic acid of claim 29.

* * * * *